US007465448B2

(12) United States Patent
Munn et al.

(10) Patent No.: US 7,465,448 B2
(45) Date of Patent: Dec. 16, 2008

(54) CHEMOKINE RECEPTOR ANTAGONISTS AS THERAPEUTIC AGENTS

(75) Inventors: David H. Munn, Augusta, GA (US); Andrew L. Mellor, Martinez, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 667 days.

(21) Appl. No.: 10/660,131

(22) Filed: Sep. 11, 2003

(65) Prior Publication Data

US 2004/0161425 A1 Aug. 19, 2004

Related U.S. Application Data

(60) Provisional application No. 60/409,804, filed on Sep. 11, 2002.

(51) Int. Cl.
*A61K 39/00* (2006.01)
(52) U.S. Cl. .................................. 424/141.1; 424/143.1
(58) Field of Classification Search ....................... None
See application file for complete search history.

(56) References Cited

U.S. PATENT DOCUMENTS

| | | | |
|---|---|---|---|
| 5,582,831 A | 12/1996 | Shinitzky | |
| 5,648,219 A | 7/1997 | MacKay et al. | |
| 5,849,589 A | 12/1998 | Tedder et al. | |
| 5,851,756 A | 12/1998 | Steinman et al. | |
| 5,871,728 A | 2/1999 | Thomson et al. | |
| 5,885,579 A | 3/1999 | Linsley et al. | |
| 5,994,126 A | 11/1999 | Steinman et al. | |
| 6,008,004 A | 12/1999 | Olweus et al. | |
| 6,080,409 A | 6/2000 | Laus et al. | |
| 6,194,204 B1 | 2/2001 | Crawford et al. | |
| 6,210,662 B1 | 4/2001 | Laus et al. | |
| 6,224,859 B1 | 5/2001 | Thomson et al. | |
| 6,228,640 B1 | 5/2001 | Cezayirli et al. | |
| 6,274,378 B1 | 8/2001 | Steinman et al. | |
| 6,290,972 B1 | 9/2001 | Armitage et al. | |
| 6,395,876 B1 | 5/2002 | Munn et al. | |
| 6,451,840 B1 | 9/2002 | Munn et al. | |
| 6,645,491 B1 | 11/2003 | Oldham et al. | |
| 2001/0001040 A1 | 5/2001 | Munn et al. | |
| 2002/0138860 A1 | 9/2002 | Cook et al. | |
| 2003/0017485 A1 | 1/2003 | Wei et al. | |
| 2003/0077247 A1 | 4/2003 | Caux et al. | |
| 2003/0140361 A1* | 7/2003 | Brennan et al. ............... 800/18 |
| 2003/0194803 A1 | 10/2003 | Munn et al. | |
| 2004/0023286 A1 | 2/2004 | Wei | |
| 2004/0042998 A1 | 3/2004 | Oldham et al. | |
| 2006/0057559 A1 | 3/2006 | Xu et al. | |
| 2006/0292618 A1 | 12/2006 | Mellor et al. | |
| 2007/0048769 A1 | 3/2007 | Mellor et al. | |

FOREIGN PATENT DOCUMENTS

| | | |
|---|---|---|
| WO | WO 99/29310 | 6/1999 |
| WO | WO 00/66764 | 11/2000 |
| WO | WO 01/17558 A2 | 3/2001 |

OTHER PUBLICATIONS

Freshney, R. I. Culture of Animal Cells, A Manual of Basic Technique, Alan R. Liss, Inc., New York, p. 3-4 (1983).*
Dermer, G. B. Another aniversary for the war on cancer. Bio/Technology, vol. 12, No. 3, p. 320 (Mar. 1994).*
Bell et al. In Breast Carcinoma Tissue, Immature Dentritic Cells Reside within the Tumor, whereas Mature Dentritic Cells are Located in the Peritumoral Areas. J. Exp Med., vol. 190, No. 10, pp. 1417-1425 (Nov. 1999).*
Kleeff et al. Detection and Localization of MIP-3alpha/LARC/Exodus, a Macrophage Proinflammatory Chemokine, and its CCR6 Receptor in Human Pancreatic Cancer. Int. J. Cell, vol. 81, pp. 650-657 (1999).*
Albert, M. L., Dendritic cell maturation is required for the cross-tolerization of CD8+ T cells, *Nature Immunol.*, 2, 1010-1017, 2001.
Alexander, A. M. et al., Indoleamine 2,3-Dioxygenase expression in transplanted NOD islets prolongs graft survival after adoptive transfer of diabetogenic splenocytes, *Diabetes*, 51:356-364, 2002.
Banchereau, J. et al., Immune and clinical responses in patients with metastatic melanoma to CD34+ progenitor- derived dendritic cell vaccine, *Cancer Res.*, 61, 6451-6458, 2001.
Bankenstein, T. et al, Cross-priming versus cross- tolerance: are two signals enough?, *Trends in Immunol.*, 23, 171-173, 2002.
Bax, A. et al., MLEV-17-based two-dimensional homonuclear magnetization transfer spectroscopy, *J. Magn. Reson.*, 65: 355-360, 1985.
Bell, D. et al., In breast carcinoma tissue, immature dendritic cells reside within the tumor, whereas mature dendritic cells are located in peritumoral areas, *J. Exp. Med.*, 190, 1417-1426, 1999.
Bennett, S. R. et al., Help for cytotoxic-T-cell responses is mediated by CD40 signalling, *Nature*, 393, 478-480, 1998.
Bodenhausen, G. et al., Natural abundance Nitrogen-15 NMR by enhanced heteronuclear spectroscopy, Natural *Chem. Phys. Lett.*, 69: 185-189, 1980.
Cady, S. G. et al., 1-Methyl-DL-tryptophan, β-(3-Benzofuranyl)-DL-alanine (the Oxygen Analog of Tryptophan), and β-[3-Benzo(b)thienyl]-DL-alanine (the Sulfur Analog of Tryptophan) are competitive inhibitors of Indoleamine 2,3-Dioxygenase, *Arch. Biochem. Biophys.*, 291, 326-333, 1991.

(Continued)

*Primary Examiner*—Marianne P. Allen
*Assistant Examiner*—Regina M DeBerry
(74) *Attorney, Agent, or Firm*—Kilpatrick Stockman LLP

(57) ABSTRACT

The present invention provides methods and compositions to reduce immune tolerance at specific sites. In one aspect, the present invention comprises methods and compositions to reduce tumorigenicity. In an embodiment, the present invention reduces recruitment of tolerance-inducing antigen presenting cells (APCs) or their precursors to a tumor and/or tumor draining lymph node by decreasing binding of at least one tumor-associated ligand to a chemokine receptor present on the tolerance-inducing APCs or APC precursors. In an embodiment, the chemokine receptor is CCR6 and the tumor-associated ligand is mip-3α. In another aspect, the present invention comprises methods and compositions to reduce immune tolerance to a virus. In an embodiment, the virus is HIV. The present invention further provides for the development of CCR6 antibodies and antagonists as therapeutic agents to prevent or reduce immune tolerance.

5 Claims, 13 Drawing Sheets
(3 of 13 Drawing Sheet(s) Filed in Color)

OTHER PUBLICATIONS

Cella, M. et al., Ligation of CD40 on dendritic cells triggers production of high levels of interleukin-12 and enhances T cell stimulatory capacity:T-T help via APC activation, *J. Exp. Med.*, 184, 747-752, 1996.

Cella, M. et al., Plasmacytoid monocytes migrate to inflamed lymph nodes and produce large amounts of type I interferon, *Nature Medicine*, 5, 919-923, 1999.

Chen, S., et al., In vivo inhibition of CC and CX3C Chemokine-induced Leukocyte infiltration and attenuation of glomerulonephritis in Wistar-Kyoto (WKY) rats by vMIP-II, *J. Exp. Med.*, 188: 193-198 (1998).

Chen, W. et al., TGF-62 released by apoptotic T cells contributes to an immunosuppressive milieu, *Immunity*, 22:14, 715-725, 2001.

Cobbold, S. et al., Infectious tolerance, *Curr. Opin. Immunol.*, 10, 518-524, 1998.

Cornilescu, G. et al., Protein backbone angle restraints from searching a database for chemical shift and sequence homology, *J. Biomol. NMR*, 13: 289-302, 1999.

Curiel, T. J. et al., Tumor immunotherapy: inching toward the finish line, *J. Clin. Invest.*, 109, 311-312, 2002.

Dhodapkar, M. V. et al., Mature dendritic cells boost functionally superior $CD8^+$ T-cell in humans without foreign helper epitopes, *J. Clin. Invest.*, 105, R9-R14, 2000.

Dhodapkar, M. V. et al., Antigen-specific inhibition of effector T cell function in humans after injection of immature dendritic cells, *J. Exp. Med.*, 193, 233-238, 2001.

Doan, T. et al., Peripheral tolerance to human papillomavirus E7 oncoprotein occurs by cross-tolerization, is largely Th-2-independent, and is broken by dendritic cell immunization, *Cancer Res.*, 60, 2810-2815, 2000.

Dong et al., B7-H1, a third member of the B7 family, co-stimulates T-cell proliferation and interleukin-10 secretion, *Nature Med.*, 5, 1365-1369, 1999.

Dzionek, A. et al., BDCA-2, BDCA-3, and BDCA-4: Three markers for distinct subsets of dendritic cells in human peripheral blood, *J. Immunol.*, 165, 6037-6046, 2000.

Facchetti, F. et al., Plasmacytoid monocytes (so-called plasmacytoid T cells) in Hodgkin's disease, *J. Pathol.*, 158, 57-65, 1989.

Fallarino, F. et al., Functional expression of indoleamine 2,3-dioxygenase by murine $CD8\alpha^+$ dendritic cells, *Internat Immunol.*, 14(1),65-68, 2002.

Fiocchi, C., TGF-β/Smad signaling defects in inflammatory bowel disease: mechanisms and possible novel therapies for chronic inflammation, *J. Clin. Invest.*, 108, 523-526, 2001.

Gallucci, S. et al., Natural adjuvants: Endogenous activators of dendritic cells, *Nat. Med.*, 5, 1249-1255, 1999.

Gorczynski, R. et al., Dendritic cells expressing TGFβ/IL-10, and CHO cells with OX-2, increase graft survival, *Transplantation Proceedings*, 33, 1565-1566, 2001.

Grohmann, U. et al., IL-6 inhibits the tolerogenic function of $CD8\alpha^+$ dendritic cells expressing indoleamine 2,3-dioxygenase, *J. Immunol.*, 167, 708-714, 2001.

Grouard, G. et al., The enigmatic plasmacytoid T cells develop into dendritic cells with interleukin (IL)-3 and CD40-ligand, *J. Exp. Med.*, 185, 1101-1111, 1997.

Heiser, A. et al., Autologous dendritic cells transfected with prostate-specific antigen RNA stimulate CTL responses against metastatic prostate tumors, *J. Clin. Invest.*, 109, 409-417, 2002.

Honey, K. et al., Dominant regulation: a common mechanism of monoclonal antibody induced tolerance?, *Immunol. Res.*, 20, 1-14, 1999.

Horuzsko, A. et al., Maturation of antigen presenting cells is compromised in HLA-G transgenic mice, *Internat Immunol.*, 13, 385-394, 2001.

Hwu, P. et al., Indoleamine 2,3-Dioxygenase production by human dendritic cells results in the inhibition of T cell proliferation, *J. Immunol.*, 164:3596-3599, 2000.

Iwasaki, A. et al., Localization of distinct peyer's patch dendritic cell subsets and their recruitment by chemokines macrophage inflammatory protein (MIP)-3α, MIP-3β, and secondary lymphoid organ chemokine, *J. Exp. Med.*, 191, 1381-1393, 2000.

Jonuleit, H. et al., Pro-inflammatory cytokines and prostaglandins induce maturation of potent immunostimulatory dendritic cells under fetal calf serum-free conditions, *Eur. J. Immunol.*, 27, 3135-3142, 1997.

Jonuleit, H. et al., Dendritic cells as a tool to induce anergic and regulatory T cells, *Trends Immunol.*, 22, 394-400, 2001.

Kikuchi, T. et al., Dendritic cells modified to express CD40 ligand elicit therapeutic immunity against preexisting murine tumors, *Blood*, 96, 91-99, 2000.

Kourilsky, P. et al., Cytokine fields and the polarization of the immune response, *Trends in Immunol.*, 22, 502-509, 2001.

Kudo, Y. et al., Human placental indoleamine 2,3-dioxygenase: cellular location and characterization of an enzyme preventing fetal rejection, *Biochem, Biophys. Acta*, 1500, 119-124, 2000.

Lee et al., Tryptophan deprivation sensitizes activated T cells to apoptosis prior to cell division, *Immunol.*, 107: 452-460 (2002).

Liu, Y. J., Dendritic cell subsets and lineages, and their functions in innate and adaptive immunity, *Cell*, 106, 259-262, 2001.

Maloy, K. G. et al., Regulatory T cells in the control of immune pathology, *Nature Immunol.*, 2, 816-822, 2001.

Mellor, A.L. et al., Prevention of T cell-driven complement activation and inflammation by tryptophan catabolism during pregnancy, *Nat. Immunol.* 2: 64-68 (2001).

Mellor, A. L. et al., Cells expressing indoleamine 2,3-dioxygenase inhibit T cell responses, *J. Immunol.*, 168, 3771-3776, 2002.

Miki, T. et al., Blockade of tryptophan catabolism prevents spontaneous tolerogenicity of liver allografts, *Transplantation Proceedings*, 33, 129-130, 2001.

Muller, A. et al, Involvement of chemokine receptors in breast cancer metastasis, *Nature*, 410: 50-56, 2001.

Munn, D. H. et al., Prevention of allogeneic fetal rejection by tryptophan catabolism, *Science*, 1191-1193, 1998.

Munn, D. H. et al., Potential regulatory function of human dendritic cells expressing indoleamine 2,3-dioxgenase, *Science*, 297, 1867-1870, 2002.

Munn, D. H. et al., Inhibition of T cell proliferation by macrophage tryptophank catabolism, *J. Exp. Med.*, 189, 1363-1372, 1999.

Neuhaus, D. et al, *The Nuclear Overhauser Effect in Structural and Conformational Analysis*, VCH New York, Chapter 8, The Two-Dimensional NOESY Experiment, 1989, pp. 253-305.

Ochsenbein, A. F. et al., Roles of tumour localization, second signals and cross priming in cytotoxic T-cell induction, *Nature*, 411, 1058-1064, 2001.

Olweus, J. et al., Dendritic cell ontogeny: A human dendritic cell lineage of myeloid origin, *Proc. Natl. Acad. Sci. USA*, 94, 12551-12556, 1997.

Palczewski, K. et al., Crystal structure of rhodopsin: A G protein—coupled receptor, *Science* 289: 739-745, 2000.

Pickl, W. F. et al., Molecular and functional characteristics of dendritic cells generated from highly purified $CD14^+$ peripheral blood monocytes, *J. Immunol.*, 157, 3850-3859, 1996.

Piotto, M. et al, Gradient-tailored excitation for single-quantum NMR spectroscopy of aqueous solutions, *J. Biomol. NMR.*, 2: 661-665, 1992.

Reddy, A. et al., A monocyte conditioned medium is more effective than defined cytokines in mediating the terminal maturation of human dendritic cells, *Blood*, 90, 3640-3646, 1997.

Ridge, J. P. et al., A conditioned dendritic cell can be a temporal bridge between a $CD4^+$ T-helper and a T-killer cell, *Nature*, 393, 474-478, 1998.

Sakaguchi, S., Regulatory T cells: key controllers of immunologic self-tolerance, *Cell*, 101, 455-458, 2000.

Sali, A. et al., Definition of general topological equivalence in protein structures, *J. Mol. Biol.*, 212, 403-428, 1990.

Schoenberger, S. P. et al., T-cell help for cytotoxic T lymphocytes is mediated by CD40-CD40L interactions, *Nature*, 393, 480-483, 1998.

Shevach, E. M., Certified professionals: CD4+CD25+ suppressor T cells, *J. Exp. Med.*, 193, F41-F45, 2001.

Shortman, K. et al., Immunity or tolerance? That is the question for dendritic cells, *Nature Immunol.*, 2, 988-989, 2001.

Shortman, K. et al., Mouse and human dendritic cell subtypes, *Nature Reviews: Immunology*, 2, 151-161, 2002.

Smyth, M. J., et al., A fresh look at tumor immunosurveillance and immunotherapy, *Nature*, 2, 293-298, 2001.

Sotomayer, E. J. et al., Cross-presentation of tumor antigens by bone marrow-derived antigen-presenting cells is the dominant mechanism in the induction of T-cell tolerance during B-call lymphoma progression, *Blood*, 98, 1070-1077, 2001.

Sozzani, S. et al., The role of chemokines in the regulation of dendritic cell trafficking, *J. Leukocyte Biol.*, 66, 1-9, 1999.

Spatola, A.F. et al, Rediscovering and endothelin antagonist (BQ-123): a self-deconvoluting cyclic pentapeptide library, *J. Med. Chem.*, 39: 3842-3846, 1996.

Spatola, A.F., Chemistry and Biochemistry of Amino Acids, Peptides, and Proteins, ed. B. Weinstein et al, New York, vol. VII, pp. 267-357, 1983.

Staveley-O'Carroll, K. et al., Induction of antigen-specific T cell anergy: An early event in the course of tumor progression, *Proc. Natl. Acad. Sci. USA*, 95, 1178-1183, 1998.

Summers, K. L. et al., Phenotypic characterization of five dendritic cell subsets in human tonsils, *Am. J. Pathol.*, 159, 285-295, 2001.

Sutmuller, R. P. M. et al., Synergism of cytotoxic T lymphocyte-associated antigen 4 blockade and depletion of CD25+ regulatory T cells in antitumor therapy reveals alternative pathways for suppression of autoreactive cytotoxic T lymphocyte responses, *J. Exp. Med.*, 194, 823-832, 2001.

Szabolcs, P. et al., Dendritic cells and macrophages can mature independently from a human bone marrow-derived, post-colony-forming unit intermediate, *Blood*, 87, 4520-4530, 1996.

Tarazona, R. et al, Effects of different antigenic microenvironments on the course of CD8+ T cell responses in vivo, *Int. Immunol.*, 8, 351-358, 1996.

Taylor, M. W. et al., Relationship between interferon-γ, indoleamine 2,3-dioxygenase, and tryptophan catabolism, *FASEB J.*, 5, 2516-2522, 1991.

Thompson, A. W. et al., Are dendritic cells the key to liver transplant tolerance?, *Immunol. Today*, 20, 27-31, 1999.

Todryk, S., A sense of tumour for the immune system, *Immunol.*, 107, 1-4, 2002.

van Elsas, A. et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation, *J. Exp. Med.*, 190, 355-366, 1999.

van Elsas, A. et al., Elucidating the autoimmune and antitumor effector mechanisms of a treatment based on cytotoxic T lymphocyte antigen-4 blockade in combination with a B16 melanoma vaccine: comparison of prophylaxis and therapy, *J. Exp. Med.*, 194, 481-489, 2001.

Varona, R. et al., CCR6-deficient mice have impaired leukocyte homeostasis and altered contact hypersensitivity and delayed-type hypersensitivity responses, *J. Clin. Invest.*, 107, R37-R45, 2001.

Waldmann, H. et al., Regulating the immune response to transplants: a role for CD4+ regulatory cells?, *Immunity*, 14, 399-406, 2001.

Wishart, D.S. et al., 1H, 13C and 15N chemical shift referencing in biomolecular NMR, *J. Biomol. NMR*, 6, 135-140, 1995.

Yang, D. et al., Cutting edge: Immature dendritic cells generated from monocytes in the presence of TGF-β1 express functional C-C chemokine receptor 6, *J. Immunol.*, 163, 1737-1741, 1999.

Zlotnik, A. et al., Chemokines: a new classification system and their role in immunity, *Immunity*, 12, 121-127, 2000.

Morita, Y. et al., Dendritic cells genetically engineered to express IL-4 inhibit murine collagen-induced arthritis, *J. Clin. Invest.*, 107, 1275-1284, 2001.

Morse, M.A. et al., Technology evaluation: Theratope, Biomira Inc., *Curr. Opin. Mol. Ther.*, Aug 2(4):453-458, 2000.

Morse, M. A. et al., Clinical applications of dendritic cell vaccines, *Current Opinion in Molecular Therapeutics*, 2(1):20-28, 2000.

Nair, S. K. et al., Induction of carcinoembroyonic antigen (CEA)-specific cytotoxic T-lymphocyte responses in vitro using autologous dendritic cells loaded with CEA peptide or CEA RNA in patients with metastic malignancies expressing CEA, *Int. J. Cancer*, 82, 121-124, 1999.

Poluektova, L. Y. et al., Generation of cytotoxic T cells against virus-infected human brain macrophages in a murine model of HIV-1 encephalitis, *J Immunol.*, 168:3941-3949, 2002.

Roncarolo, M. G. et al., Differentiation of T regulatory cells by immature dendritic cells, *J. Exp. Med.*, 193, F5-F9, 2001.

Yoon, J.-W. et al., Control of autoimmune diabetes in NOD mice by GAD expression or suppression of β cells, *Science*, 284, 1183-1187, 1999.

Basheer, R. et al., "Adenosine as a biological signal mediating sleepiness following prolonged wakefulness," Biol. Signals Recept., 9(6): 319-327 (2000) (Abstract only).

Bonner, James A. et al., "Radiotherapy plus Cetuximab for Squamous-Cell Carcinoma of the Head and Neck," New England Journal of Medicine, 354(6): 567-578 (2006).

Broaddus, V. Courtney et al., "Neutralization of IL-8 Inhibits Neutrophil Influx in a Rabbit Model of Endotoxin-Induced Pleurisy," Journal of Immunology, 152: 2960-2967 (1994).

Bursill, Christina A. et al., "Membrane-Bound CC Chemokine Inhibitor 35K Provides Localized Inhibition of CC Chemokine Activity in Vitro and In Vivo," The Journal of Immunology, 177: 5567-5573 (2006).

Casilli, Federica et al., "Inhibition of interleukin-8 (CXCL8/IL-8) responses by repertaxin, a new inhibitor of the chemokine receptors CXCR1 and CXCR2," Biochemical Pharmacology, 69: 385-394 (2005).

Coiffier, Bertrand, "Monoclonal antibody as therapy for malignant lymphomas," C.R. Biologies, 329: 241-254 (2006).

Cunningham, M.D., David et al., "Cetuximab Monotherapy and Cetuximab plus Irinotecan in Irinotecan-Refractory Metastatic Colorectal Cancer," New England Journal of Medicine, 351: 337-345 (2004).

Dieu, Marie-Caroline et al., "Selective Recruitment of Immature and Mature Dendritic Cells by Distinct Chemokines Expressed in Different Anatomic Sites," J. Exp. Med., 188: 373-386 (1998).

Feldmann, Marc and Ravinder N. Maini, "Anti-TNFα Therapy of Rheumatoid Arthritis: What Have We Learned?," Annu. Rev. Immunol., 19: 163-196 (2001).

Hart, T. K. et al., "Preclinical efficacy and safety of pascolizumab (SB 240683): a humanized anti-interleukin-4 antibody with therapeutic potential in asthma," Clin. Exp. Immunol., 130: 93-100 (2002).

Kaminski, Mark S. et al., "Radioimmunotherapy of B-Cell Lymphoma with [$^{131}$I] Anti-B1 (Anti-CD20) Antibody," New England Journal of Medicine, 329: 459-465 (1993).

Lin, Michael Z. et al., "The Evolution of Antibodies into Versatile Tumor-Targeting Agents," Clinical Cancer Research, 11: 129-139 (2005).

Munn, David H. et al., "Expression of indoleamine 2,3-dioxygenase by plasmacytoid dendritic cells in tumor-draining lymph nodes," The Journal of Clinical Investigation, 114(2): 280-290 (2004).

Munn, David H. et al., "GCN2 Kinase in T Cells Mediates Proliferative Arrest and Anergy Induction in Response to Indoleamine 2,3-Dioxygenase," Immunity, 22: 633-642 (2005).

Pandi-Perumal, S. R. et al., "Melatonin: Nature's most versatile biological signal?" FEBS Journal, 273: 2813-2838 (2006).

Piccart-Gebhart, M.D., Martine J. et al., "Trastuzumab after Adjuvant Chemotherapy in HER2-Positive Breast Cancer," New England Journal of Medicine, 353(16): 1659-1672 (2005).

Ramchandani, Shyam et al., "DNA methylation is a reversible biological signal," Proc. Natl. Acad. Sci. USA, 96: 6107-6112 (1999).

Slamon, M.D., Dennis J. et al., "Use of Chemotherapy Plus a Monoclonal Antibody Against HER2 For Metastatic Breast Cancer that Overexpresses HER2," New England Journal of Medicine, 344(11): 783-792 (2001).

Uno, Tomoyasu et al., "Eradication of established tumors in mice by a combination antibody-based therapy," Nature Medicine, 12(6): 693-698 (2006).

Yang, D. et al., "β-Defensins: Linking Innate and Adaptive Immunity Through Dendritic and T Cell CCR6," Science, 286: 525-528 (1999).

Yang, James C. et al., "A Randomized Trial of Bevacizumab, an Anti-Vascular Endothelial Growth Factor Antibody, for Metastatic Renal Cancer," New England Journal of Medicine, 349(5): 427-434 (2003).

Zangemeister-Wittke, Uwe, "Antibodies for Targeted Cancer Therapy- Technical Aspects and Clinical Perspectives," Pathobiology, 72: 279-286 (2005).

Zou, Weiping et al., "Stromal-derived factor-1 in human tumors recruits and alters the function of plasmacytoid precursor dendritic cells," Nature Medicine, 7(12): 1339-1346 (2001).

Baban et al., "A Minor Population of Splenic Dendritic Cells EXpressing CD19 Mediates IDO-Dependent T Cell Suppression Via Type 1 IFN Signaling Following B7 Ligation," *International Immunology*, 2005 17(7): 909-919.

Bjorck et al , "Isolation and characterization of plasmacytoid dendritic cells from Flt3 ligand and granulocyte-macrophage colony-stimulating factor-treated mice" *Blood*, 2001, 98(13): 3520-3526.

Borras et al., "Identification of Both Myeloid CD11c and Lymphoid CD11c Dendritic Cell Subsets in Cord Blood," *British Journal of Haematology*, 2001, 113: 925-931.

Cady et al., "1-Methyl-DL-tryptophan, beta-(3benzofuranyl)-DL-alanine (the oxygen analog of tryptophan), and beta-3-benxo(b)thienyll-DL-alanine (the sulfur analog of tryptophan) are competitive inhibitors for indoleamine 2,3-dioxygenase," *Archives of Biochemistry and Biophysics*, 1991, 291(2): 326-333 (Abstract).

Chapman et al., "Pharmacologically active benzo'bl thiophene derivatives. VIII Benzo'bl thiophene analogs of tryptophan and alpha-methyltryptophan, and some of their 5-substituted derivatives," *Journal of the Chemical Society, Section C: Organic Chemistry*, 1969, No. 14: 1855-1858 (Abstract).

Dagher et al., "Pilot Trial of Tumor-Specific Peptide Vaccination and Continuous Infusion Interleukin-2 in Patients with Recurrent Ewing Sarcoma and Alveolar Rhabdomyosarcoma: An Inter-Institute NIH Study," *Med. Pediatr. Oncol.*, 2002, 38: 158-164.

Friberg et al., "Indoieamine 2,3-Dioxygenase Contributes to Tumor Cell Evasion of T Cell-Mediated Rejection," *Int. J Cancer*, 2002, 101: 151-155.

Friberg et al., "Indoleamine 2,3-dioxygenase (IDO) protects established tumors from T cell mediated rejection," *Proc. Amer. Ass Cancer Res. Ann. Meet.*, 2000, No. 714, p. 112 (Abstract).

Frumento et al., "Inhibition of T cell proliferation by the purified enzyme indoleamine 2,3-dioxygenase," *Human Immunology, The European Federation for Immunogenetics 14th Annual Conference*, Apr. 4-7, 2000, 61: p. S140 (Abstract).

Grohmann et al. "IFN-γ Inhibits Presentation of a Tumor-Sell Peptide by CD8a- Dendritic Cells Via Potentiation of the CD8a+ subset" *Journal of Immunology*, 2000, 165(3): 1357-1363.

Hwu et al., "Indoleamine 2,3-Dioxygenase Production by Human Dendritic Cells Results in the Inhibition of T Cell Proliferation" *J. Immunol.*, 2000, 164. 3596-3599.

Lee et al., "Pattern of Recruitment of Immunoregulatory Antigen-Presenting Cells in Malignant Melanoma," *Laboratory Investigation*, 2003, 83(10) 1457-1466.

Mellor et al., "Extinguishing Maternal Immune Responses during Pregnancy: Implications for Immunosuppresion," *Seminars in Immunology*, 2001, 13(4): 213-218.

Mellor et al., "Tryptophan catabolism and T cell tolerance immunosuppression by starvation?" *Immunology Today*, 1999, 20 469-473.

Mellor et al., "Tryptophan catabolism prevents maternal T cells from activating lethal anti-fetal immune responses," *J. Reprod. Immunol.*, 2001, 52(1-2): 5-13.

Mellor et al , "HLA-G transgenic mice." *J. Reprod. Immunol.*, 1999, 43: 253-261.

Mellor et al , "Immunology at the maternal-fetal interface," *Ann. Rev. Immunol.*, 2000, 18: 367-391.

Mellor et al., "IDO expression by dendritic cells tolerance and tryptophan catabolism" *Nat. Immunol. Rev.*, 2004, 4: 762-774.

Munn et al., "Ligation of B7-1/B7-2 by Human CD4+ T Cells Triggers Indoleamine 2,3-Dioxygenase Activity in Dendritic Cells," *Journal of Immunology*, 2004, 172: 4100-4110.

Munn et al., "Dendritic Cells Have the Option to Express IDO-Mediated Suppression or Not," *Blood*, 2005, 105(6). 2618.

Munn et al., "Macrophage inhibition of T cell activation via depletion of tryptophan," *Blood*, 1998, 48-IV, (Abstract).

Munn et al., "Potential Regulatory Function of Human Dendritic Cells Expressing Indoleamine 2,3-Dioxygenase." *Science*, 2002, 297 1867-1870.

Munn et al., "Regulation of T cell activation by macrophage (Mvariant phi)-mediated tryptophan (TRP) depletion," *FASEB Journal*, 1998, 12: p. A276 (Abstract).

Munn et al., "Tolerogenic Antigen-Presenting Cells," *Ann. NY. Acad. Sci.*, 2002 961: 343-345.

Osugi et al., "Myeloid Blood CD11c+ Dendritic Cells and Monocyte-Derived Dendritic Cells Differ in their Ability to Stimulate T Lymphocytes." *Blood*, 2002, 100(8): 2858-2866.

Pacanowski et al., "Reduced blood CD123+ (lymphoid) and CD11c+ (myeloid) dendritic cell numbers in primary HIV-1 infection" *Blood*, 2001, 98(10) 3016-3021.

Peterson et al., "Evaluation of functionalized tryptophan derivatives and related compounds as competitive inhibitors of indoleamine 2,3-dioxygenase," *Medicinal Chemistry Research*, 1994, 3(6): 531-544 (Abstract).

Potula et al., "Inhibition of Indoleamine 2,3-Dioxygenase (IDO) Enhances Elimination of Virus-Infected Macrophages in an Animal Model of HIV-1 Encephalitis," *Blood*, 2005, 106(7): 2382-2390.

Reddy et al., "A monocyte conditioned medium is more effective than defined cytokines in mediating the terminal maturation of human dendritic cells" *Blood*, 1997, 90(9): 3640-3646.

Romani et al , "Generation of mature dendritic cells from human blood" *Immunol. Meth.*, 1996, 196: 137-151.

Southan et al., "Structural requirements of the competitive binding site of recombinant human indoleamine 2,3-dioxygenase," *Medicinal Chemistry Research*, 1996, 6(5): 343-352 (Abstract).

Tan et al., "Creation of Tolerogenic Human Dendritic Cells via Intracellular CTLA4: A Novel Strategy with Potential in Clinical Immunosuppression," *Blood*, 2005, 106(9). 2936-2943.

Tan et al., "Modulation of human dendritic cell function following transduction with viral vectors; implications for gene therapy," *American Society of Hematology, Blood First Edition Paper*, prepublished online Jan. 25, 2005.

Terness et al., "Regulation of Human Auto-and Alloreactive T Cells by Indoleamine 2,3-Dioxygenase (IDO)-Producing Dendritic Cells. Too Much Ado about IDO?" *Blood*, 2005, 105(6): 2480-2486.

Terness et al., "The Immunoregulatory Role of IDO-Producing Dendritic Cells Revisited," *Trends in Immunology*, 2006, 27 68-73.

Yoshida et al, "Tryptophan Degradation in Transplanted Tumor Cells Undergoing Rejection," *Journal of Immunology*, 1988, 141(8) 2819-2823.

\* cited by examiner

SEQUENCE LISTING

<160> NUMBER OF SEQ ID NOS: 1

<210> SEQ ID NO 1
<211> LENGTH: 18
<212> TYPE: PRT
<213> ORGANISM: Homo sapiens

<400> SEQUENCE: 1

Asp Leu Ile Glu Ser Gly Gln Leu Arg Glu Arg Val Glu Lys Leu Asn
1               5                   10                  15

Met Leu

CHEMOKINE RECEPTOR ANTAGONISTS AS THERAPEUTIC AGENTS

RELATED APPLICATIONS

This application claims priority to Provisional Application 60/409,804, filed Sep. 11, 2002. The entire disclosure of Provisional Application 60/409,804, is incorporated in its entirety herein.

FEDERAL FUNDING

The studies described herein were supported at least in part by Federal grants from the National Institutes of Health (NIH R01 HL60137; NIH R01 HL57930; NIH R01 AI44219; NIH R21 AI49849; NIH R21 AI44759; NIH CA 103220; and NIH K08 HL03395), the National Institutes of Health and National Cancer Institute (NIH/NCI/RAID), and the Mason Trust Foundation. Thus, the Federal government may have rights in this invention.

NOTICE OF COPYRIGHT PROTECTION

A section of the disclosure of this patent document and its figures contain material subject to copyright protection. The copyright owner has no objection to the facsimile reproduction by anyone of this patent document, but otherwise reserves all copyright rights whatsoever.

FIELD OF THE INVENTION

The invention relates to the use of compounds that block recruitment of tolerance-inducing antigen presenting cells (APCs) to sites requiring an immune response. As an example, the present invention comprises the use of agents that bind to the CCR6 receptor present on tolerance-inducing APCs to block recruitment of tolerance-inducing APCs to a tumor.

BACKGROUND OF THE INVENTION

Once established, human tumors are not rejected by the immune system, a state of functional tolerance which eventually proves fatal to the host (Smyth, M. J., et al., *Nat. Immunol.* 2, 293 (2001)). Evidence from murine models suggests that immunologic unresponsiveness may arise when tumor-associated antigens are presented by certain bone marrow-derived tolerogenic (tolerance-producing) antigen-presenting cells (APCs) (Sotomayor, E. M., et al., *Blood,* 98: 1070-1077 (2001); Doan, T., et al., *Cancer Res.,* 60: 2810-2815 (2000)). Conversely, in the setting of tissue transplantation, it would be desirable to isolate and administer such tolerogenic APCs.

However, in humans and mammals other than mice, the identity of tolerogenic APCs, and the mechanisms they use to induce tolerance, remain elusive. Thus, in humans, "immature" myeloid dendritic cells (DCs) have been postulated to function as tolerizing APCs based on findings that these cells: (1) have a decreased ability to stimulate T cell responses in vitro (Reddy, A., et al., *Blood,* 90: 3640-3646 (1997); Jonuleit, H., et al., *Eur. J. Immunol.,* 27: 3135-3142 (1997)); (2) may promote the function of immunosuppressive or "regulatory" T cells (Tregs) following prolonged co-incubation (Jonuleit, H., et al., *Trends Immunol.,* 22: 394-400 (2001)); and (3) have the ability to abrogate antigen-specific T cell responses in vivo (Dhodapkar, M. V., et al., *J. Exp. Med.,* 193: 233-238 (2001); see also U.S. Pat. Nos. 5,871,728 and 6,224,859). However, the molecular mechanism used by immature DCs or other putative tolerogenic APCs to suppress T cell responses is unclear.

Other findings indicate that maturation of DCs is not necessarily associated with abrogation of T cell suppression and/or tolerance (Albert, M. L., *Nature Immunol.,* 2: 1010 (2001); Shortman, K. et al., *Nature Immunol.,* 2: 988-989 (2001); T. Bankenstein and T. Schuler, *Trends in Immunol.,* 23: 171-173 (2002)). Instead, there may be an as yet undefined signal that acts after T cells have received the signals of antigen presentation and co-stimulation from a fully mature APC which then diverts the T cells to activation or tolerance. In this model, the tolerogenic phenotype is independent of the maturation status of the APC (in fact, maturation enhances tolerance induction) and depends instead on an intrinsic attribute of the APC.

It would be desirable to prevent tolerogenic APCs from inducing tolerance where such tolerance is not therapeutically beneficial, as for example, at the site of a tumor or a tumor draining lymph node. Thus, it would be desirable to prevent the migration of tolerogenic APCs to sites, such as tumors, where they are detrimental, while still allowing for migration of non-tolerogenic (i.e., activating) APCs to these sites.

SUMMARY OF THE INVENTION

Embodiments of the present invention recognize that tolerance-inducing (suppressive) antigen-presenting cells (APCs) may express certain cytokine receptors on their surface whereas non-tolerogenic APCs may express a different complement of cytokine receptors on their surface. For example, in one embodiment, the cytokine receptor that is preferentially expressed on tolerogenic APCs is CCR6. The present invention also recognizes that the agents that prevent binding of cytokine receptors expressed on the tolerogenic APCs to a ligand present at the site of APC recruitment may be used to reduce immune tolerance in a subject.

For example, in an embodiment, the present invention comprises administering a composition to a subject to reduce recruitment of tolerance-inducing antigen-presenting cells (APCs) or their precursors to a site of APC recruitment in the subject.

In another embodiment, the present invention comprises a method to reduce tumorgenicity in a subject comprising administering a composition to the subject to reduce recruitment of tolerance-inducing antigen-presenting cells (APCs) or their precursors to a tumor and/or a tumor draining lymph node in the subject.

In yet another embodiment, the present invention comprises a method to determine whether a compound comprises an antagonist of tolerance-inducing APCs comprising measuring whether the compound reduces migration of tolerance-inducing APCs or their precursors towards a biological signal for APC recruitment.

In another embodiment, the present invention comprises a composition to reduce immune tolerance in a subject comprising a compound that reduces tolerance-inducing antigen-presenting cells (APCs) or their precursors at site of APC recruitment in the subject.

There are many advantages associated with the present invention. For example, in an embodiment, the present invention provides methods and compositions to reduce immune tolerance in a subject at sites where tolerance is detrimental.

Also, the present invention provides methods and compositions for enhancing the immune response by preventing migration of tolerogenic APCs to a site requiring an immune response.

The present invention may be used to enhance the immune response to tumors, infectious agents, and/or other pathologies that may trigger inflammation or an immune response. In an embodiment, recruitment of tolerogenic APCs to a tumor and/or a tumor draining lymph node may reduced. For example, the present invention provides methods and compositions to prevent migration of tolerogenic APCs that express the CCR6 chemokine receptor to tumors that express a ligand for CCR6. Additionally, and/or alternatively, recruitment of tolerogenic APCs to a site of viral infection may be reduced.

There are additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
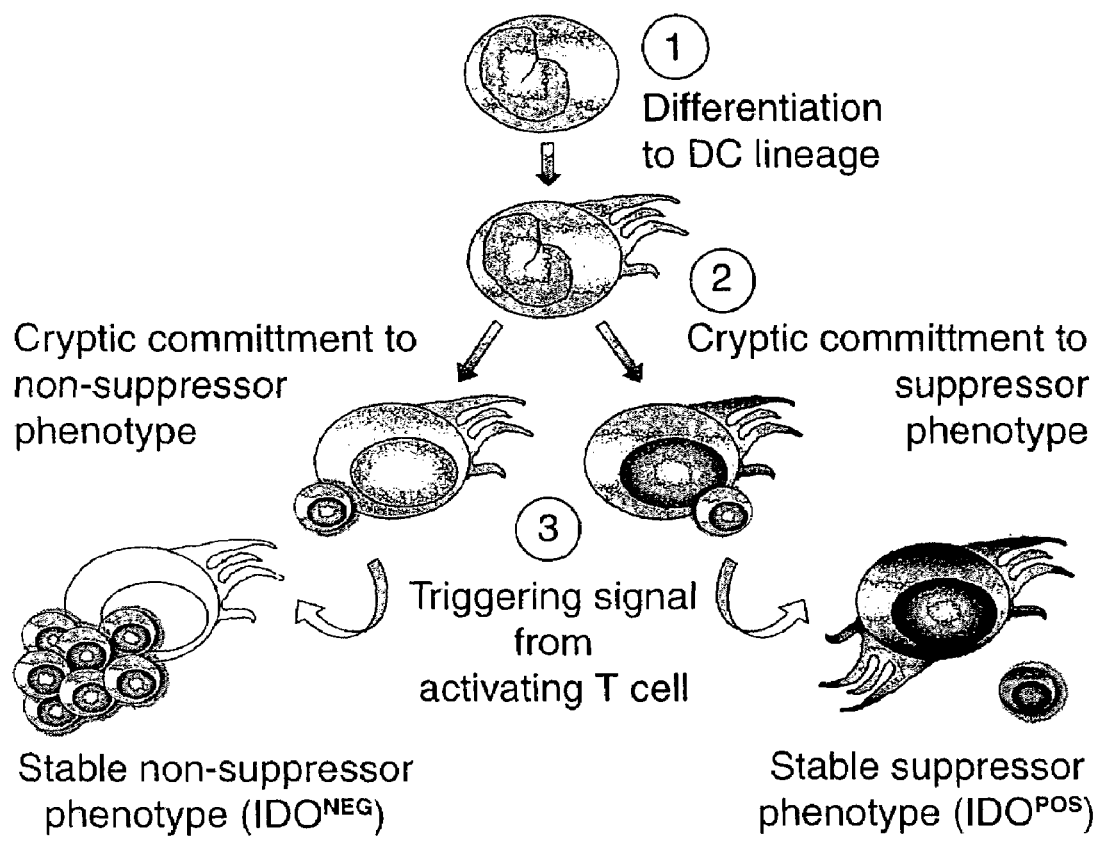
FIG. 1 shows a schematic representation of a 3-step model for the regulation of IDO during dendritic cell (DC) differentiation in accordance with an embodiment of the present invention.

The present invention describes methods and compositions to reduce immune tolerance at specific sites. In one aspect, the present invention comprises methods and compositions to reduce tumorigenicity. In another aspect, the present invention comprises methods and compositions to reduce immune tolerance to an infectious agent, such as a virus. In an embodiment, the virus is HIV. Thus, embodiments of the present invention provide for reducing recruitment of tolerance-inducing antigen presenting cells (APCs) or their precursors to a tumor and/or tumor draining lymph node, a site of infection, or other sites of inflammation and/or immune response, by decreasing binding of at least one ligand present at the site of APC recruitment to a cell surface protein present on the tolerance-inducing APCs or APC precursors. In an embodiment, the cell surface protein on the tolerance-inducing APC is the CCR6 chemokine receptor and the ligand is mip-3α. The present invention further describes the development of CCR6 antagonists as therapeutic agents to prevent or reduce immune tolerance In an embodiment, the present invention comprises a method to reduce immune tolerance in a subject. In an embodiment, the method comprises administering a composition to the subject to reduce recruitment of tolerance-inducing antigen-presenting cells (APCs) or their precursors to a site of APC recruitment in the subject.

In other embodiments, the present invention comprises a composition to reduce immune tolerance in a subject comprising a compound that reduces recruitment of tolerance-inducing antigen-presenting cells (APCs) or their precursors to a site of APC recruitment in a subject. In an embodiment, the composition further comprising a pharmaceutically acceptable carrier.

In an embodiment, the tolerance-inducing APCs express elevated levels of indoleamine 2,3-dioxygenase (IDO). In an embodiment, the level of IDO enzyme activity expressed by the tolerance-inducing APCs is sufficient to suppress proliferation of T cells. The enzyme indoleamine 2,3-dioxygenase (IDO) is an intracellular heme-containing enzyme that catalyzes the initial rate-limiting step in tryptophan degradation along the kynurenine pathway. Thus, in one embodiment, tolerance is mediated by the enzyme indoleamine 2,3-dioxygenase (IDO). Thus, in an embodiment, expression of IDO is associated with depletion of local tryptophan, thus leading to a reduced activation of T cells.

The subject for which reduced immune tolerance is desired may be mammalian. In an embodiment, the subject is human.

A variety of factors may determine the levels of a subject's immune response.

The present invention, however, recognizes that there may be a specific interaction between molecules (such as proteins, and other signaling agents) present at the site of APC recruitment and the tolerance inducing APCs or their precursors. Thus, the present invention recognizes that tolerance inducing APCs or their precursors may be selectively recruited to a site by biological signals expressed during the inflammatory response. The present invention thus describes blocking that interaction as a means to reduce immune tolerance. In an embodiment, the composition comprises a compound that blocks the interaction between a biological signal present at the site of APC recruitment and a protein expressed on the surface of the tolerance-inducing antigen-presenting cells (APCs) or their precursors.

For example, in an embodiment, the compound at the site of APC recruitment may bind to, or otherwise interact with, proteins expressed on the surface of the tolerance inducing APC or its precursor. For example, certain tumors express the chemotaxis factor mip-3α. Thus, in one embodiment, the biological signal present at the site of APC recruitment may comprise mip-3α.

Tolerance-inducing APCs may express various proteins on the surface of the cell. Thus, in an embodiment of the present invention, the protein expressed on the surface of the tolerance-inducing antigen-presenting cells (APCs) or their precursors may comprise a chemokine receptor. In a further embodiment, the chemokine receptor may comprise CCR6. For example, mip-3α comprises a ligand for the CCR6 chemokine receptor.

For example, where the APC comprises cell surface CCR6, the compound used to block the interaction between the tolerance inducing APCs or their precursor and a ligand at the site of APC recruitment may comprise an antibody to CCR6. Alternatively, and/or additionally, the compound used to block the interaction between the tolerance inducing APCs or their precursor and a ligand at the site of APC recruitment may comprise a CCR6 antagonist. In yet another embodiment, the compound used to block the interaction between the tolerance inducing APCs or their precursor and a ligand at the site of APC recruitment may comprise a CCR6 inverse agonist. In yet another embodiment, the compound used to block the interaction between the tolerance inducing APCs or their precursor and a ligand at the site of APC recruitment may comprise an antibody to the ligand present at the site of APC recruitment. Thus, in an embodiment, antibodies to mip-3α may be used.

The methods and compositions of the present invention may be used to reduce immune tolerance that is caused by various pathologies. Thus, in an embodiment, the site of APC recruitment for which the recruitment of tolerant cells is inhibited comprises a tumor. Alternatively, and/or additionally, the site of APC recruitment may comprise a site of infection. In an embodiment, the viral infection may comprise human immunodeficiency virus (HIV).

APCs are also recruited to lymphoid tissue(s) which may be active in mediating the subject's immune reaction. Thus, in an embodiment, the site of APC recruitment comprises lymphoid tissue. For example, the site of APC recruitment may comprise lymphoid tissue draining a tumor. Alternatively, the site of APC recruitment may comprise lymphoid tissue draining a site of infection.

Thus, in an embodiment, the present invention comprises a method to improve the a subject's ability to reject a tumor. For example, in one embodiment, the present invention comprises a method to reduce immune tolerance to a tumor in a subject comprising administering a composition to the subject to reduce recruitment of tolerance-inducing antigen-presenting cells (APCs) or their precursors to a tumor and/or a tumor draining lymph node in the subject. In an embodiment, the subject is human.

A variety of biological signals may promote migration of tolerance-inducing APCs to the site of a tumor or a tumor draining lymph node. In an embodiment, the composition comprises a compound that reduces binding of a ligand expressed by the tumor to a chemokine receptor expressed on the surface of the tolerance-inducing antigen-presenting cells (APCs) or their precursors. In an embodiment, the ligand comprises mip-3α, although other tumor-associated ligands may be targeted. Also, in an embodiment, the chemokine receptor comprises CCR6.

The present invention also comprises a method to identify compounds that may be used to reduce immune tolerance. For example, the present invention comprises a method to determine whether a compound comprises an antagonist of tolerance-inducing APCs. Thus, in an embodiment, the present invention comprises a method to identify a compound for reducing recruitment of tolerance-inducing antigen-presenting cells (APCs) or their precursors to a signal for APC recruitment comprising measuring whether the compound reduces migration of tolerance-inducing APCs or their precursors towards a biological signal for APC recruitment.

The method may further comprise the steps of identifying the tolerance-inducing antigen-presenting cells (APCs) that express levels of indoleamine 2,3-dioxygenase (IDO) enzyme activity sufficient to suppress proliferation of T cells; identifying at least one of the biological signals that recruits tolerance-inducing APCs; adding a test compound; and measuring whether the compound reduces migration of the identified tolerance-inducing APCs to the signal for APC recruitment.

The present invention recognizes that proteins on the surface of tolerance inducing APCs may be interacting with biological signals expressed at the site of APC recruitment to provide for selective recruitment of the tolerance inducing APCs. Thus, in one embodiment of the method, the tolerance inducing APCs are more fully characterized to determine the identity of at least one protein expressed on the cell surface of the tolerance inducing APCs recruited to the site. Also, the method may comprise determining whether the protein(s) present on the surface of the tolerance-inducing APC binds to the signal present at the site of APC recruitment. In this way, and in a further embodiment of the present invention, the profile of cell surface proteins may be used to identify putative targets for compounds that reduce recruitment of tolerance-inducing APCs.

In an embodiment, a chemotaxis factor, such as a chemokine receptor ligand comprises the signal for APC recruitment. In an embodiment, mip-3α is the biological signal at the site of recruitment. Mip-3α is a ligand for the CCR6 chemokine receptor. Thus, in an embodiment, the protein expressed on the tolerance inducing APC comprises a chemokine receptor. For example, the protein expressed on the tolerance inducing APC may comprise the CCR6 chemokine receptor. For example, the compound to reduce immune tolerance may comprise an antibody to CCR6. Alternatively, the compound to reduce immune tolerance may comprise a small molecule CCR6 antagonist.

Thus, in an embodiment, the compound for reducing recruitment of tolerance-inducing antigen-presenting cells (APCs) or their precursors to a signal for APC recruitment at least partially inhibits binding of the biological signal present at the site of recruitment to a chemokine receptor expressed on the surface of the tolerance-inducing antigen-presenting cells (APCs) or their precursors. For example, in an embodiment, the signal for biological recruitment comprises mip-3α and the chemokine receptor expressed by the APCs is CCR6.

The in vitro tests may be verified by in vivo studies. Thus, in an embodiment, the method further comprises testing the ability of the compound to inhibit migration of tolerance-inducing antigen-presenting cells (APCs) or their precursors to a tumor draining lymph node, but does not inhibit migration of the tolerance-inducing antigen-presenting cells (APCs) or their precursors to at least one non-tumor draining lymph node.

$IDO^+$ and $IDO^{LO}$ APCs

The present invention recognizes that myeloid-derived antigen-presenting cells (APCs) which are enriched for tolerance-inducing APCs, or depleted of tolerance-inducing APCs, can be isolated and used for various therapeutic applications. See commonly owned, co-pending application Ser. No. 10/121,909, filed Apr. 12, 2002, and incorporated by reference in its entirety herein. Thus, the inventors have discovered that antigen-presenting cells may be separated into a tolerance-inducing population, which is associated with high levels of expression of the enzyme indoleamine-2,3-dioxygenase ($IDO^+$), and a T cell activating (non-tolerance-inducing) population, which is associated with low levels of expression of IDO ($IDO^{LO}$) (U.S. patent application Ser. No. 10/121,909; Munn et al., Science, 297:1867-1870, 2002). Moreover, which of these two types of APC predominates may depend on the physiological environment to which the APCs are exposed. Thus, in many cases, a contaminating admixture of the undesired type of APC (i.e. $IDO^{LO}$ vs. $IDO^+$) may render the APC population unusable, or even harmful, for the desired application. For example, if the goal is to generate tolerance toward donor histocompatability antigens prior to organ transplantation, exposure to activating ($IDO^{LO}$) cells could promote worsened rejection. Conversely, if the goal is to enhance responses to weak tumor antigens, the presence of $IDO^+$ tolerance-inducing cells may suppress the desired response (see e.g., Grohmann, U., et al., J. Immunol. 167: 708-714 (2001), for studies in murine model).

Thus, the present invention recognizes that APCs expressing high levels of the intracellular enzyme indoleamine 2,3-dioxygenase ($IDO^+$) are capable of suppressing T cell responses in vitro and in vivo. Thus, in an embodiment, tryptophan-degrading enzyme indoleamine 2,3-dioxygenase (IDO) may comprise an intrinsic attribute of APCs that determines whether or not the APC is immunosuppressive or immunostimulatory. As described herein, the present invention provides a means to alter recruitment of immunosuppressive APCs (i.e. $IDO^+$ APCs) to a specific site.

Immunologic tolerance may comprise a reduced immunologic rejection response toward specific tissues or antigens. Conceptually, tolerance may be understood as comprising (at least) two types of tolerance: pre-existing tolerance to self, and acquired tolerance to new antigens. For example, imunocompetent mice can become anergic (non-reactive) even to non-self antigens when these antigens are introduced on tumors (Staveley-O'Carroll, K., et al., Proc. Natl. Acad. Sci. USA, 95: 1178-1183 (1998)). This anergy is apparently caused not by the tumor cells themselves, but by cross-presentation of tumor antigens by tolerogenic bone marrow-derived APCs (Sotomayor, E. M., et al., *Blood*, 98: 1070-1077 (2001)).

Tolerogenic APCs can be potent regulators of the immune response because they can create networks of immunoregulatory (suppressor) T cells. These regulatory T cell networks may be involved in maintaining normal tolerance to self, and also in mediating a state of acquired unresponsiveness to non-self antigens (e.g. Sakaguchi, S., *Cell,* 101: 455-459 (2000); H. Waldmann and S. Cobbold, *Immunity,* 14: 399-406 (2001); Shevach, E. M., *J. Exp. Med.,* 193: F41-F46 (2001)). For example, it has been shown that tumor-specific regulatory T cells exist, and that blocking or depleting these cells facilitates the ability to break tolerance to tumor antigens (Sutmuller, R. P. M., et al., *J. Exp. Med.,* 194: 823-832 (2001); van Elsas, A., et al., *J. Exp. Med.,* 190: 355-366 (1999); van Elsas, A., et al., *J. Exp. Med.,* 194: 481-490 (2001)). Once established, this type of unresponsiveness is self-perpetuating, transferable, and can even "spread" to encompass new antigens encountered in the same context as those to which the network is already tolerant (S. Cobbold and H. Waldmann, *Curr. Opin. Immunol.,* 10: 518-524 (1998)). When present, regulatory T cells tend to be dominant, enforcing functional tolerance throughout the entire immune system even in the face of other, non-tolerant T cells (Honey, K., et al., *Immunol. Res.,* 20: 1-14 (1999)). It is known that certain types of human APCs are able to promote such regulatory T cells (Jonuleit, H., *Trends in Immunol.* 22: 394-400 (2001); Dhodapkar, M. V., et al., *J. Exp. Med.,* 193: 233-238 (2001)). However the mechanism by which this occurs is unknown. Clearly, the ability to create such potent regulatory T cells is highly desirable in settings such as organ transplantation or autoimmunity. Conversely, it is undesirable (but often occurs) to inadvertently create such cells when immunizing against antigens (e.g. from pathogens or tumors).

The enzyme indoleamine 2,3-dioxygenase (IDO) is an intracellular heme-containing enzyme that catalyzes the initial rate-limiting step in tryptophan degradation along the kynurenine pathway (M. W. Taylor and G. Feng, *FASEB J.,* 5, 2516-2522 (1991)). It has been proposed that IDO suppresses T cell proliferation by degrading tryptophan in the local environment (Munn, D. H., et al., *J. Exp. Med.,* 189: 1363-1372 (1999)). Two types of human APCs, (1) monocyte-derived macrophages (Munn, D. H., et al., *J. Exp. Med.,* 189: 1363-1372 (1999)), and (2) monocyte-derived dendritic cells (Hwu, P., et al., *J. Immunol.* 164: 3596-3599 (2000)), which suppress T cell activation in vitro have been shown to express the tryptophan-degrading enzyme indoleamine 2,3-dioxygenase (IDO). In mice, IDO has been implicated in the tolerance displayed by the maternal immune system toward the immunologically disparate fetus (Mellor, A. L., et al., *Nat. Immunol.* 2: 64-68 (2001); Munn, D. H., et al., *Science,* 281: 1191-1193 (1998)), as well as in acquired tolerance toward antigens presented by murine CD8α$^+$ dendritic cells (Grohmann, U. et al., *J. Immunol.,* 167: 708-714 (2001)). Also, IDO is required for the induction of spontaneous tolerance by liver allografts (Miki, T., et al., *Transplantation Proceedings* 33: 129-130 (2000)), a process which is thought to be mediated by graft associated DCs (Thompson, A. W. and Lu., L., *Immunol. Today* 20: 27-31 (1999)). A direct mechanistic link between IDO gene expression and suppression of antigen-specific T cell responses in vivo has been shown in a mouse model by the inventors (Mellor, A. L., et al., *J. Immunol.* 168: 3771-3776 (2002)), wherein transfection of the mouse IDO gene into murine cell lines causes: (1) suppression of T cell responses to antigens presented by the IDO-expressing cell lines; and (2) abrogation of the ability of the cells to prime an allogenic T cell response in vivo to antigens.

There are several ways to measure IDO expression. Cells comprising elevated or high levels of IDO activity may comprise: (1) a level of IDO activity sufficient to suppress T cell proliferation either in vitro or in vivo; (2) a level of IDO protein or RNA significantly above the background level of the assay; or (3) at least 90% of APCs in the preparation expressing IDO as enumerated on a cell-by-cell basis. For example, in an embodiment, elevated or high level IDO expression (IDO$^+$) is defined by flow cytometry quantitatively on a cell by cell basis as expression of antigenic IDO protein at a level of at least 2-fold above background. In a further embodiment, elevated or high level IDO expression (IDO$^+$) comprises expression of IDO protein at a level of at least 5-fold above background. In yet a further embodiment, IDO$^+$ cells may comprise IDO protein at a level of at least 10-fold over background. Background may be defined as neutralization of an anti-IDO antibody using standard techniques such as binding with an excess of an immunizing peptide (polyclonal antibody assay) or binding of an isotype-matched control (monoclonal antibody assay). Thus, in an embodiment of the present invention, tolerance-inducing IDO$^+$ APCs (i.e., having elevated IDO) comprise at least 90% of the APC population expressing IDO at levels of at least 2-fold over background, and more preferably, at least 95% of the APC population expressing IDO at levels of at least 2-fold over background.

Preferably, using the techniques of immunohistochemistry or in situ hybridization, IDO expression is measured on a cell-by-cell basis. Cells expressing IDO are defined relative to the appropriate negative control for the particular assay as understood by one skilled in the art. Preferably, APCs expressing elevated IDO comprise at least 90% of the APC population in such an assay, an more preferably, at least 95% of the APC population.

IDO can also be measured by quantifying IDO protein and RNA levels by techniques including, but not limited to, western blot, immunohistochemistry, northern blot, reverse-transcriptase polymerase chain reaction (RT-PCR), in situ hybridization, and other assays that measure IDO in a bulk population. In an embodiment, elevated or high level IDO expression (IDO$^+$) for a bulk population is defined as an IDO-specific signal of at least 2-fold over the negative control for the particular assay as understood by one skilled in the art. In a further embodiment, elevated or high level IDO expression (IDO$^+$) for a bulk population is defined as an IDO-specific signal of at least 5-fold over background. In yet a further embodiment, elevated or high level IDO expression (IDO$^+$) for a bulk population is defined as an IDO-specific signal of at least 10-fold over background.

Conversely, low levels of IDO expression (IDO$^{LO}$) may be defined by flow cytometry or other assays quantitatively on a cell-by-cell basis with reference to the percentage of cells expressing IDO. Thus, in an embodiment, IDO$^{LO}$ cells comprise APCs wherein a minority of APCs in the preparation express IDO protein at a level of at least 2-fold over background. In an IDO$^{LO}$ preparation of APCs, preferably less than 10% of the APCs express IDO protein at a level of at least 2-fold over background. More preferably less than 5% of the APCs express IDO protein at a level of at least 2-fold over background in an IDO$^{LO}$ preparation of APCs. Alternatively, IDO is measured by immunohistochemistry, in situ hybridization or other techniques that measure IDO on a cell-by-cell basis, and an IDO$^{LO}$ preparation is defined as comprising less than 20% IDO-expressing cells, or more preferably less than 10% IDO-expressing cells, and even more preferably, less than 5% IDO-expressing cells. Alternatively, IDO expression is measured in a bulk population, such that the IDO-specific signal is less than 2-fold over the negative control for the particular assay.

Alternatively, an assay to measure biological activity such as a T cell proliferation assay is used to quantify IDO activity.

A T cell proliferation assay includes, but is not limited to, a mixed leukocyte reaction (MLR) assay, or stimulation of T cells with antigen or mitogen.

Thus, in an embodiment, high level IDO expression (IDO$^+$) is defined as a greater than 2-fold increase in T-cell proliferation when an inhibitor of IDO is added to MLRs containing the preparation of interest. This assay provides a physiological basis to quantify the amount of T-cell proliferation that has been suppressed by IDO (i.e. the MLR without the IDO inhibitor compared to the MLR with the IDO inhibitor). Preferably, the MLR contains an APC preparation to be administered plus allogeneic or xenogeneic T cells. Alternatively, the T cell proliferation assay may contain an APC preparation to be administered plus autologous T cells and an antigen or mitogen to serve as the stimulus for T cell proliferation. Thus, high level IDO expression (IDO$^+$) may be defined as a greater than 2-fold increase in T cell proliferation when an inhibitor of IDO is added to co-cultures containing the preparation of interest.

T cell proliferation assays may also be used to quantify low IDO activity. Thus, in an embodiment, low IDO activity (IDO$^{LO}$) is defined by an allogenic MLR or autologous antigen or mitogen-stimulation assay as less than 1.5 fold increase in T cell proliferation when an inhibitor of IDO is added to co-cultures containing the APC preparation of interest.

An inhibitor of IDO is an agent capable of preventing tryptophan degradation and/or kynurenine production by IDO enzyme in a cell free system, or by cells expressing IDO. For example, the inhibitor of IDO is an agent capable of preventing tryptophan degradation and/or kynurenine production by isolated human monocyte-derived macrophages activated by interferon-γ (Munn, D. H., et al., *J. Exp. Med.*, 189: 1363-1372 (1999)). Preferably, the inhibitor of IDO is an analogue of tryptophan. More preferably, the inhibitor of IDO is the (D) isomer analogue of tryptophan rather than the (L) analogue, as in some cases only the (D) isomer reveals true suppression of T-cell activation by IDO. Thus in an embodiment, the inhibitor of IDO comprises 1-methyl-(D,L)-tryptophan, β-(3-benzofuranyl)-DL-alanine (the oxygen analog of tryptophan) (1-MT), β-[3-benzo(b)thienyl]-(D,L)-alanine (the sulfur analog of tryptophan) (S. G. Cady and M. Sono, *Arch. Biochem. Biophys.* 291, 326 (1991)), or 6-nitro-(D,L)-tryptophan. More preferably, the inhibitor of IDO comprises 1-methyl-(D)-tryptophan or 6-nitro-(D)-tryptophan.

In an embodiment, APCs or APC progenitors may comprise mature blood-derived dendritic cells, mature tissue dendritic cells, monocyte-derived macrophages, non-dendritic APCs, B cells, plasma cells, or any mixture thereof. In an embodiment, the isolated APCs or APC progenitors comprise a cell type bearing markers of antigen presentation and costimulatory function.

Non-dendritic APCs may comprise cells from peripheral blood, bone marrow, or solid organ or tissue, or cells derived by in vitro culture of cells from peripheral blood, bone marrow, or solid organ or tissue, which do not express CD83, but which do express high levels of MHC class II antigen as well as at least one marker of APC function. Such markers of APC function include, but are not limited to, CD80, CD86, and B7-H1 (Dong et al., *Nature Med.*, 5: 1365-1369 (1999)). Such non-dendritic APCs may express high constitutive or inducible levels of IDO (IDO$^+$), low levels of IDO (IDO$^{LO}$), or may comprise a mixture of IDO$^+$ and IDO$^{LO}$ cells. Non-dendritic APCs include, but are not limited to, endothelial cells, tissue macrophages, and other cells expressing constitutive or inducible MHC II.

In an embodiment, non-dendritic APCs include cultured blood-derived non-dendritic APCs. As defined herein, cultured blood-derived non-dendritic APCs comprise peripheral blood mononuclear cells or a fraction thereof which following culture in vitro, do not express CD83 but do express high levels of MHC class II antigens as well as one or more markers of APC co-stimulatory function, such as, but not limited to, CD80, CD86 or B7-H1 (Dong et al., *Nature Med.*, 5: 1365-1369 (1999)), either constitutively or following exposure to maturation agents. Blood-derived non-dendritic APCs may be cultured in a medium with or without cytokines including, but not limited to, MCSF, GMCSF, IL4, IL3, IL 10, and TNFα. For example, monocyte derived macrophages cultured in MCSF express high levels of IDO (IDO$^+$) (Munn, D. H., et al., *J. Exp. Med.*, 189: 1363-1372 (1999)). In contrast, CD14+/CD83− cells following culture in GMCSF+IL4 (which differentially adhere to plastic culture dishes) may show no IDO mediated suppression (IDO$^{LO}$).

In an embodiment, dendritic cells (DCs) may comprise cells from peripheral blood, bone marrow, organs or tissues, or derived by culture of cells isolated from peripheral blood, bone marrow, organs, tissues, or isolated CD34$^+$ stem cells collected from peripheral blood or bone marrow, which cells express CD83 constitutively or following culture and maturation. DCs may be cultured in medium with or without cytokines, including, but not limited to GMCSF, IL4, IL3, and IL10.

In an embodiment, immature dendritic cells (DCs) comprise DCs which express low levels of MHC class II antigens. As defined herein, low levels of MHC class II antigens may comprise levels less than 2-fold greater than the negative control used in the assay to measure MHC class II antigen expression. Low levels of MHC class II may also be determined by comparison to mature DCs, and preferably comprise less than half the level of expression of MHC class II antigens found on mature DCs. MHC class II antigens may be measured by flow cytometry or other methods known in the art.

In an embodiment, mature dendritic cells (DCs) comprise DCs which constitutively express high levels of MHC class II, or which have been treated with agents to cause maturation. In an embodiment, high levels of MHC class II antigens comprise levels at least 2-fold greater than the negative control used in the assay to measure MHC class II antigen expression. Maturation can also be defined by comparison with the same population of DCs prior to treatment with agents to induce maturation. Defined in this way, maturation may comprise at least a 2-fold upregulation of MHC class II antigen. Agents causing maturation comprise TNFα, CD40-ligand (CD40L), activating anti-CD40 antibodies, cells engineered to express cell surface CD40-ligand, or bacterial or pathogen products.

Also in an embodiment, B cells comprise cells from blood, bone marrow, lymph nodes or other tissue which express one or more markers of B cell differentiation such as, but not limited to, CD19, CD20, CD21, or surface immunoglobulin, wherein B cell markers may be measured by flow cytometry or other methods known in the art.

Also in an embodiment, plasma cells may comprise cells isolated from blood, lymph node or other tissue which express CD38 and cytoplasmic immunoglobulin as measured by flow cytometry or other methods known in the art.

T cell responses comprise allogeneic, xenogeneic, mitogen-driven, or antigen-driven responses. As defined herein, allogeneic T cells comprise T cells from a different individual of the same species, wherein such T cells proliferate in response to the presence of antigenic differences between the individuals. Xenogeneic T cells comprise T cells from an individual of a different species, wherein such T cells proliferate in response to the presence of antigenic differences between the species. As an example, T cells from a human recipient are xenogeneic to a porcine tissue donor.

As described in commonly owned application Ser. No. 10/121,909, APCs which comprise IDO$^+$ APCs or IDO$^{LO}$ APCs may be selected from a population of IDO$^+$/IDO$^{LO}$ cells by selective culturing of the cells, including a predetermined regimen of cytokines and/or maturation agents. For example, a cytokine cocktail such as those known in the art (Jonuleit, H., et al., *Eur. J. Immunol.,* 27: 3135-3142 (1997)) may be employed. Thus, for selection of IDO$^+$ APCs or IDO$^{LO}$ APCs, cytokines may be combined singly, or added together with other agents used for the maturation of DCs (Jonuleit, H., et al., *Eur. J. Immunol.* 27: 315-3142 (1997); Reddy, A., et al., *Blood* 90: 3640-3646 (1997)). Selection may also comprise physical selection techniques such as selective immunosorting of either IDO$^+$ or IDO$^{LO}$ cells. This is possible in that certain cell-surface antigens are associated with the IDO$^+$ and IDO$^{LO}$ phenotypes in APCs. In another embodiment, sorting comprises differential adherence of either IDO$^{lo}$ or IDO$^+$ cells to a substrate, presumably due to the expression of a specific cell surface marker that increases adherence.

The present invention provides methods to alter recruitment of tolerance-inducing IDO$^+$ APCs to a site of APC recruitment in vivo. A site of APC recruitment may comprise a biological site in a subject which provides some type of signal that signals the mobilization of APCs to that site. For example, in an embodiment, a site of recruitment comprises a site requiring or triggering an immune response. In an embodiment, a site of APC recruitment may comprise a tumor. Alternatively, a site of APC recruitment may comprise a tumor draining lymph node. In yet another embodiment, a site of APC recruitment may comprise a site of infection or inflammation. In yet another embodiment, a site of APC recruitment may comprise a lymphoid tissue draining a site of infection. The infection may be an persistent infection cause by a virus, bacteria, fungus, protozoa, or any other type of infectious microorganism. As used herein, a persistent infection is an infection which is not cleared from a subject within about 14 days of the initial infection. In an embodiment, the infection may comprise human immunodeficiency virus (HIV). Also, in an embodiment, the site of recruitment may comprise lymphoid tissue draining the site of a vaccine injection.

As discussed herein, APCs recruited to a site may comprise tolerogenic IDO$^+$ APCs. In some cases, even a relatively small percentage of IDO$^+$ APCs in a population of APCs may compromise the immune response. For example, tolerogenic IDO$^+$ APCs may reduce the subject's ability to develop an immune response to tumor cells or a viral infection. Thus, in an embodiment, the present invention provides a means to selectively reduce recruitment of tolerogenic IDO$^+$ APCs to a site.

In an embodiment, IDO expression on APCs is associated with the expression of specific cell surface markers. For example, IDO expression on APCs may associated with the expression of specific chemokine receptors. Thus, the present invention recognizes that ligands that recognize markers expressed by APCs may be involved in recruiting APCs to various sites. For example, mip-3α is a ligand for the chemokine receptor CCR6 and may be expressed by certain tumor cells. In an embodiment, CCR6 is expressed with a high degree of specificity on tolerogenic IDO$^+$ APCs, but is expressed at very low levels, or not at all, on T-cell activating IDO$^{LO}$ APCs. Thus, tumor cells that express mip-3α may be able to selectively recruit IDO$^+$ APCs to the site of a tumor, thus promoting tolerance to the tumor. In an embodiment, the present invention provides methods and compositions to block binding of mip-3α to CCR6 as a means to reduce recruitment of tolerogenic IDO$^+$ APCs to a tumor site.

FIG. 1 provides a 3-step model for the regulation of IDO expression of indoleamine 2,3-dioxygenase (IDO) in monocyte-derived dendritic cell (DC) differentiation. As described above, IDO catalyzes the initial rate-limiting step in tryptophan degradation in the kynurenine pathay and thus, it is proposed that high levels of IDO may reduce T cell proliferation by reducing tryptophan in the local environment. In step 1 of the model, monocytes begin to differentiate along the DC lineage. Step 2 occurs during later DC differentiation and maturation, when there is a cryptic commitment of each individual DC to subsequently express high levels of IDO to become either IDO$^+$, or to express low levels of IDO to become IDO$^{LO}$. In an embodiment, those DCs that commit to becoming IDO-negative (IDO$^{LO}$) are also negative for the cell surface marker CD123, suggesting that there is some degree of inherent heterogeneity or "pre-commitment" within in the circulating monocyte pool. In contrast, cells that are CD123 positive (CD123$^+$) still have the option to become either functionally IDO$^{+/POS}$ or IDO$^{LO}$, based on the conditions present during maturation. In an embodiment, the CD123$^+$ cells will commit to the IDO$^{LO}$ (non-suppressor) phenotype if step 2 is driven solely by pro-inflammatory factors (e.g., CD40L, TNFα). If counter-regulatory cytokines such IL10 or TGFβ are present during maturation, then the CD123$^+$ cells may commit to the IDO$^+$ (suppressor) phenotype.

Although the cells may be committed at step 2, in an embodiment, the functional IDO$^+$ phenotype may not be manifest until the DCs are activated, as for example, by the cytokine interferon-γ and possibly additional signals that may originate from the T cell during antigen presentation (step 3). Thus, although the same signal is delivered to both "non-suppressor" and "suppressor" DCs, the response of the DC to this signal, either IDO-mediated suppression of T-cell activation (IDO$^+$), or downregulation of IDO (IDO$^{LO}$) such that the DC able to promote T-cell activation, may depend on its history in step 2.

The model shown in FIG. 1 is consistent with existing models under which DCs undergo a "licensing" or "conditioning" process (corresponding to Step 2), either through direct cell-cell interaction with a helper T cell (Cella, M., et al., *J. Exp. Med.,* 184: 747-752 (1996); Ridge, J. P., et al., *Nature* 393: 474-478 (1998); Schoenberger, S. P., et al., *Nature* 393: 480-483 (1998); Bennett, S. R., et al, *Nature* 393: 478-480 (1998)) or via signals from the local cytokine milieu (Gallucci, S., et al., *Nat. Med.* 5: 1249-1255 (1999); Kourilsky, P,. et al., *Trends in Immunol.,* 22: 502-509 (2001)). One of the previously undescribed aspects of DC maturation that is explained by the model in FIG. 1 is that DCs can be "licensed" to suppress, and that ability of DCs to become suppressive may be regulated in vitro by culture conditions.

Additionally, the model teaches that suppressive and non-suppressive DC populations can be distinguished by IDO expression and cell surface markers associated with IDO$^+$ and/or IDO$^{LO}$ phenotypes. In vivo, the cytokines driving commitment to the suppressor phenotype (e.g., IL10, TGFβ) may be provided by interaction with regulatory T cells (H. Waldmann and S. Cobbold, *Immunity* 14: 399-406 (2001); Maloy, K. G., et al., *Nature Immunol.,* 2: 816-822 (2001)) or may be present in a generalized tolerogenic milieu (Kourilsky, P. et al., *Trends in Immunol.,* 22: 502-509 (2001); Fiocchi, C., *J. Clin. Invest.,* 108: 523-526 (2001); Chen, W. et al., *Immunity* 22:14:715-725 (2001); Jonuleit, H. et al., *Trends in Immunol.* 22: 394-400 (2001)). In vitro, the regulatory cytokines may be supplied as recombinant cytokines during maturation.

Cell Surface Markers Used to Identify IDO+ Cells

The present invention provides methods and compositions to alter recruitment of immunosuppressive APCs to specific sites comprising signals for APC recruitment. The ability to select for, or against, immunosuppressive APCs is based on the discovery that a specific subset of chemokine receptors found on tolerogenic APCs (i.e. IDO$^+$ APCs) may be used to control migration of tolerogenic (i.e. IDO$^+$) APCs to a specific site. Alternatively, a specific subset of chemokine receptors found on T-cell activating APCs (i.e. $IDO^{LO}$ APCs) may be used to control migration of activating (i.e. $IDO^{LO}$) APCs to a specific site. Thus, the present invention teaches that the ability of such receptors to promote chemotaxis of these cells to specific sites may be utilized to control immunosuppressive activity at specific sites.

APCs may be treated in vitro by culturing under selection steps to mimic the selection of $IDO^+$ and $IDO^{LO}$ APCs in vivo. For example, conditions to select for APCs that express high levels of IDO ($IDO^+$ APCs) may comprise culturing in medium which is essentially free of serum, or in the presence of macrophage colony stimulating factor (MCSF) or granulocyte-macrophage colony stimulating factor (GMCSF). Alternatively (or additionally), the cells may be cultured in the presence of cytokines such as, but not limited to, $TGF\beta$, IL10, IL 4, IL3, or any combinations thereof. Also, the cells may be treated with an agent to cause maturation of those APCs that express high levels of IDO. Such maturation agents may comprise $TNF\alpha$, IL10, $TGF\beta$, CD40-ligand, activating anti-CD40 antibodies, cells engineered to express cell surface CD40-ligand, proinflammatory bacterial or pathogen products, or any combination thereof (Munn et al., Science 297, 1867 (2002); U.S. patent application Ser. No. 10/121,909).

Figure 2:
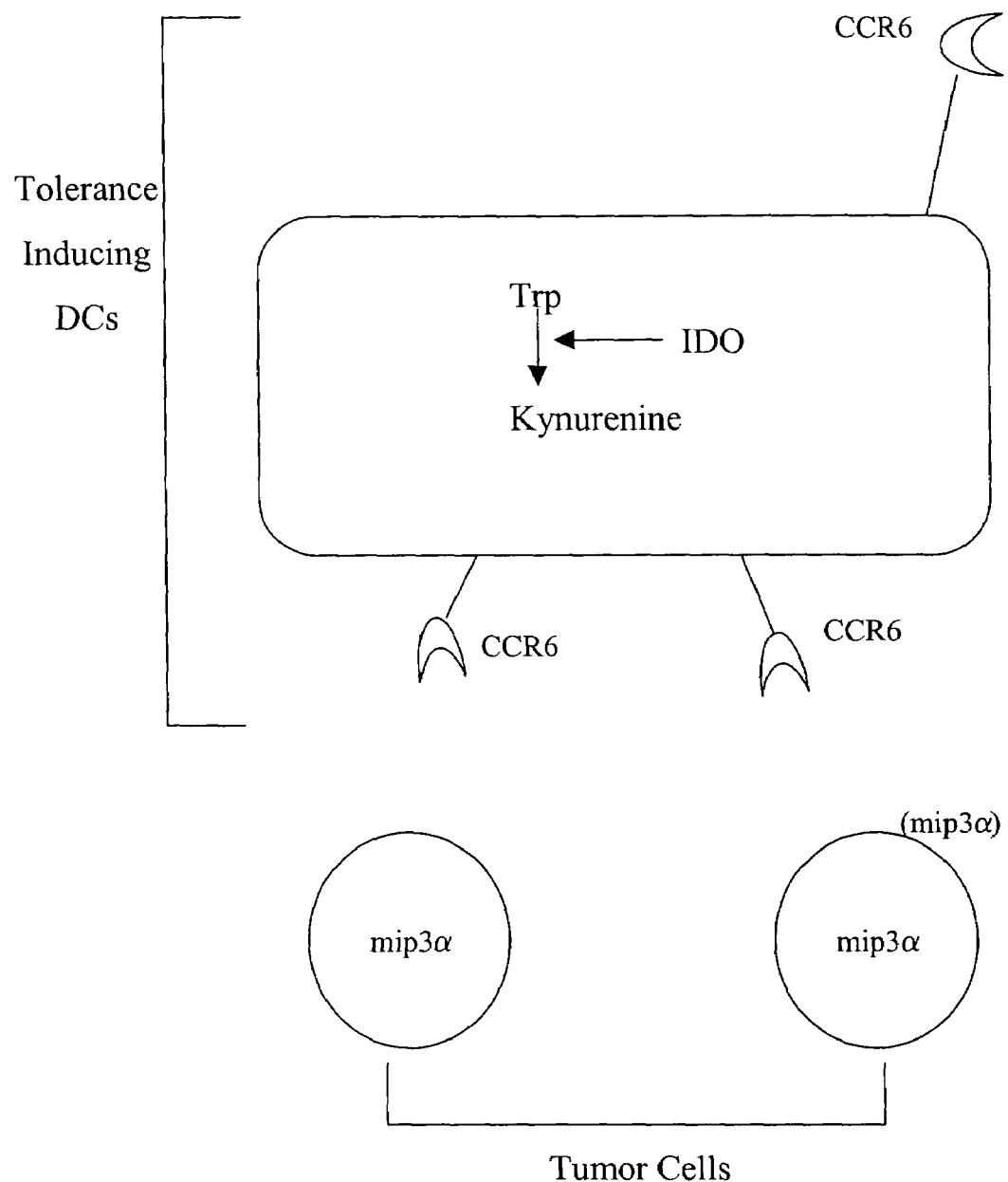
FIG. 2 shows a schematic representation of tolerance-inducing antigen-presenting cells (APCs) comprising expression of intracellular indoleamine 2,3-dioxygenase (IDO) and the chemokine receptor CCR6 juxtaposed next to tumor cells that express mip-3α, in accordance with an embodiment of the present invention.

Referring now to FIG. 2, in an embodiment, at least one cell surface antigenic marker identifies the cells as expressing high levels of IDO ($IDO^+$ APCs) or low levels of IDO ($IDO^{LO}$ APCs). In a further embodiment, the absence or presence of the cell surface marker associated with high IDO may be used to select for $IDO^+$ APCs from $IDO^{LO}$ APCs. Markers associated with high levels of IDO in APCs may comprise CCR6. Alternatively, and/or additionally, markers associated with high levels of IDO in APCs may comprise CD123 (not shown). Alternatively, and/or additionally, markers associated with high levels of IDO in APCs may comprise CD11c (not shown). Conversely, the presence of a cell-surface marker associated with low levels of IDO expression ($IDO^{LO}$) is used to select for $IDO^{LO}$ APCs. In an embodiment, a marker associated with low levels of IDO in APCs is CD14.

Thus, the present invention utilizes the discovery that specific cell surface markers are associated with expression of IDO in antigen-presenting cells (FIG. 2). In an embodiment, for markers associated with cells having high levels of IDO expression ($IDO^{30}$), the marker (e.g., CCR6) preferably comprises is a cell surface protein (antigen) for which greater than 75% of the cells express high levels of IDO by flow cytometry or suppression of T cell proliferation as measured using T cell proliferation assays. In other embodiments, the marker preferably comprises a cell surface protein (antigen) for which greater than 90% of the cells express high levels of IDO by flow cytometry or suppression of T cell proliferation as measured using T cell proliferation assays. In other embodiments, the marker preferably comprises is a cell surface protein (antigen) for which greater than 95% of the cells express high levels of IDO by flow cytometry or suppression of T cell proliferation.

Figure 3:
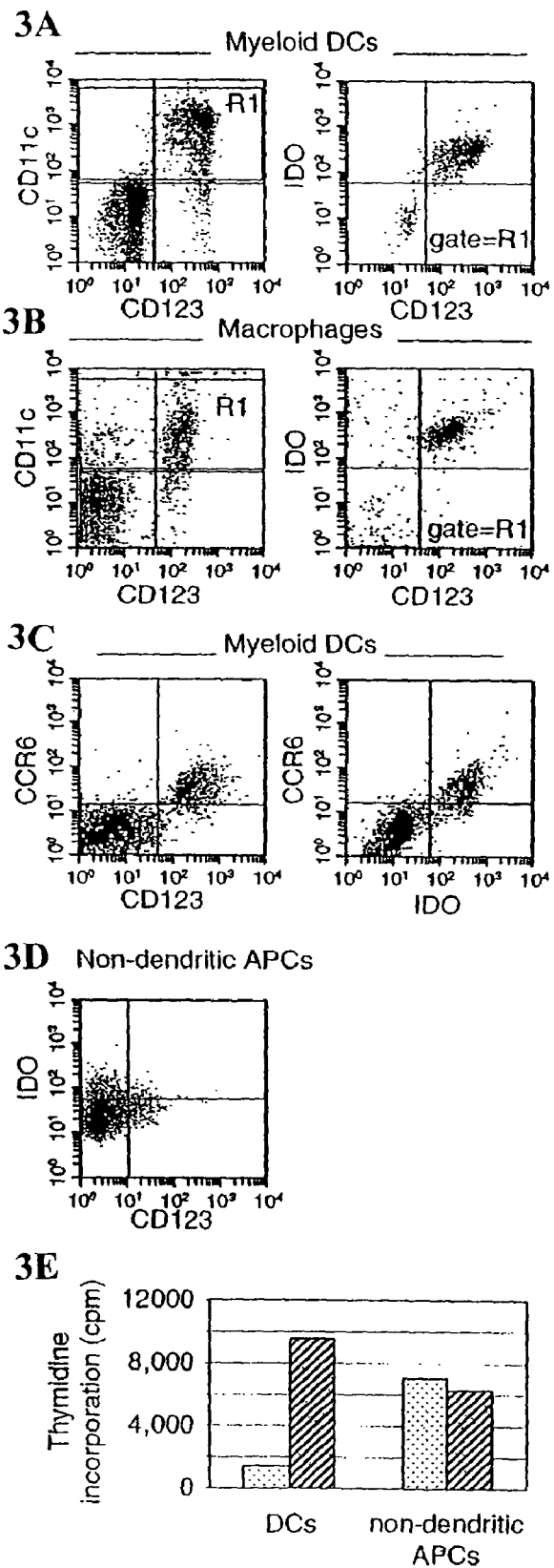
FIG. 3 shows expression of CD123, CD11c the chemokine receptor CCR6, and indoleamine 2,3-dioxygenase (IDO) by antigen-presenting cells in accordance with an embodiment of the present invention. In panels (A) and (B), human monocytes were cultured to produce myeloid dendritic cells (A) or macrophages (B), and then both groups received interferon-γ during the final 18 hrs of culture and harvested cells were triple-stained for CD123, CD11c and IDO. In (A) and (B), panels on the right show expression of IDO and CD123 in the gated CD11c$^+$ population shown on the left. In (C), myeloid dendritic cells, cultured as in panel (A), were triple-stained for CD123, IDO, and the chemokine receptor CCR6. Both panels show the entire (ungated) population. In (D), the adherent (non-dendritic) population of APCs is shown, taken from a culture similar to panel (A) but using serum-free conditions. Cells were stained for IDO and CD123. Panel (E) compares IDO-mediated suppression by DCs and non-dendritic APCs from the same culture where IDO-mediated suppression is the difference in thymidine incorporation in T cells in the absence (stippled bars) vs. the presence (striped bars) of 1-methyl-(D,L)-tryptophan (1-MT).

Referring now to FIG. 3, in an embodiment, cultured blood-derived APCs derived in bovine serum based medium may be treated to produce a preparation comprising a mixture of $IDO^+$ and $IDO^{LO}$ cells. In an embodiment, a population of immature DCs which express the cell surface marker CD123 ($CD123^+$) constitutively express immunoreactive IDO protein (FIGS. 3A and C for myeloid DCs derived in GMCSF+ IL4; FIG. 3B for macrophages derived in MCSF, respectively). Maturation for 2 days with $TNF\alpha$, or with CD40L, or with a published cocktail of cytokines (Jonuleit H., et al., Eur. J. Immunol., 27: 3135-3142 (1997), or monocyte-condition medium (Reddy et al., Blood 90: 3640-3646 (1997)) does not affect IDO expression in the subset of CD123+ cells (not shown). In an embodiment, CD123 positive ($CD123^+$) cells expressing high levels of IDO ($IDO^+$) also express high levels of the cytokine receptor CCR6 (FIG. 3C). In contrast, cells selected as adhering to the culture dishes comprise primarily $IDO^{LO}$ non-dendritic APCs (FIG. 3D). Preferably, expression of IDO protein correlates with the ability of the cells to stimulate T cell proliferation as measured by tritiated thymidine incorporation into T cell DNA (FIG. 3E).

Figure 5:
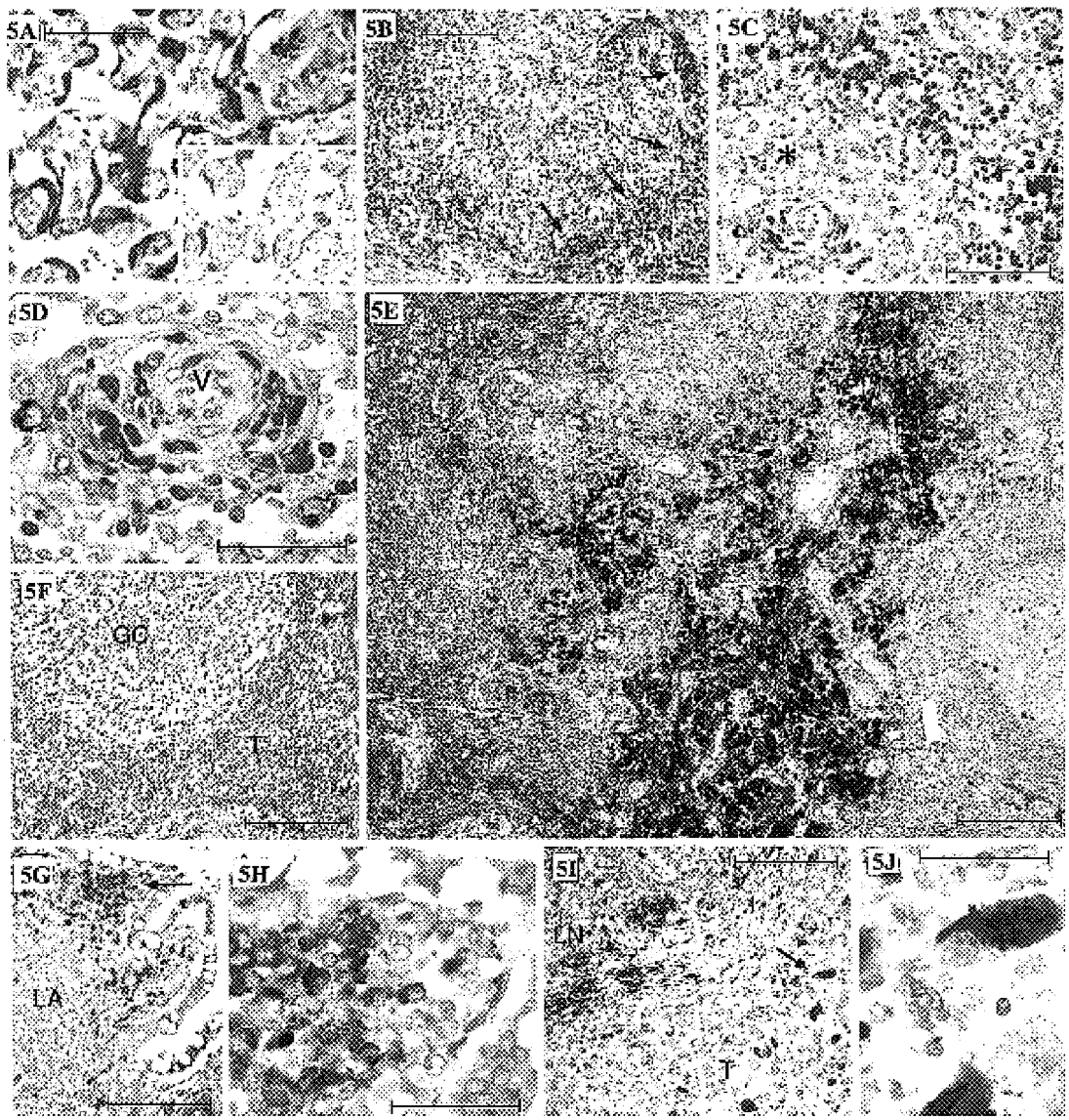
FIG. 5 shows detection of IDO-expressing (IDO$^+$) CD123$^+$ dendritic cells in human tumors and draining lymph nodes in accordance with an embodiment of the present invention. Panel (A) shows a positive control for IDO (brown) in syncytiotrophoblast cells of term human placenta (inset: the same tissue, but with anti-IDO antibody neutralized by an excess of the immunizing peptide and shown at half scale). Panel (B) shows a malignant melanoma primary cutaneous tumor stained for IDO (arrows) (Fast Red chromogen). Panel (C) shows a draining lymph node of a malignant melanoma, showing accumulation of IDO-expressing cells (red) in the lymphoid and perivascular regions of the node, but sparing the macrophage-rich sinuses (asterisk). Panel (D) shows a higher magnification of panel (C), with a characteristic collection of IDO-expressing cells (dark signal) around a high-endothelial venule (V). Panel (E) shows a low-power view of a draining lymph node containing heavily pigmented metastatic melanoma cells and/or abnormal collections of melanin-laden macrophages (black; darkest signal), with confluent infiltration of IDO-expressing cell (red; next darkest signal) around the tumor/macrophage deposits. Panel (F) shows normal lymphoid tissue with scattered IDO$^+$ cells (red; scattered dark signals) in a germinal center (GC) and T cell regions (T) of a human pharyngeal tonsil from a routine tonsillectomy. Panels (G) and (H) (higher magnification of the region in panel (G) indicated by the arrow) shows co-localization of cells expressing IDO (brown; darkest cytoplasmic signal) and mip-3α (red; next darkest cytoplasmic signal) in the lamina propria of the small intestine, particularly in the subepithelial areas overlying mucosal lymphoid aggregates (LA). Panels (I) and (J) (higher magnification of the region in panel (I) indicated by the arrow) shows expression of mip-3α (red) by tumor cells in a lesion of malignant melanoma metastatic to lymph node, such that the mip-3α$^+$ cells are scattered throughout the tumor (arrow) (T), while the IDO$^+$(brown) cells are congregated at the margins of the metastasis but confined to the residual lymph node tissue (LN).

Preferably there is a 1: correspondence between APCs expressing IDO ($IDO^+$) and at least one cell surface marker. For example, in an embodiment, monocyte-derived DCs cultured for 7 days in GMCSF+IL4 (FIG. 3A) or macrophage-derived DCs cultured in MCSF (FIG. 3B) display a discrete subset of cells that express high levels of IDO ($IDO^+$), and express the cell surface marker CD123 and CCR6 (FIGS. 5A and B).

In an embodiment, the marker highly associated with IDO expression is the chemokine receptor CCR6. CCR6 is the receptor for the chemokine mip-3α, a chemotactic factor for immature dendritic cells (Yang, D., et al., J. Immunol., 163: 1737-1741 (1999)). Different subsets of dendritic cells express distinct patterns of chemokine receptors (Sozzani, S., et al., J. Leukocyte Biol. 66: 1-9 (1999)). CCR6 is expressed on $CD34^+$-derived dendritic cells at immature stages of differentiation, and on immature monocyte-derived dendritic cells cultured with transforming growth factor (TGF)-β, but is lost under some conditions when dendritic cells mature (Yang, D., et al., J. Immunol. 163: 1737-1741 (1999)). In an embodiment, under conditions favoring high expression of IDO, over 90% of APCs which express IDO also express CCR6 (FIG. 3C).

Alternatively, and/or additionally, another cell surface marker that may be associated with IDO expression is CD123. CD123 (the IL3-receptor α chain) is expressed on the small population of lymphoid-lineage "plasmacytoid" dendritic cells in peripheral blood (Liu, Y. J., Cell, 106: 259-262 (2001)), but it is also expressed at lower levels on a poorly-defined subset of myeloid-lineage dendritic cells in vivo (Olweus, J., et al., Proc. Natl. Acad. Sci., USA, 94: 12551-12556 (1997); Summers, K. L., et al., Am. J. Pathol., 159: 285-295 (2001)).

Other cell surface markers may be used to identify $IDO^+$ cells. Thus, in an embodiment, a majority of $IDO^+$ APCs express the myeloid-lineage marker CD11c (FIGS. 3A and B). Thus, in an embodiment, IDO-expressing, tolerance-inducing APCs may comprise the cell surface markers CD123, CCR6, and in some cases, CD11c.

In an embodiment, the specific pattern of markers that identifies the $IDO^+$ (or $IDO^{LO}$) population varies depending on the biological signal which triggers generation of the APC population. For example, CD11c is expressed at low levels in $IDO^{LO}$ cells cultured in bovine calf serum based medium but is expressed at higher levels for the $IDO^{LO}$ culture in serum-free medium.

Enrichment using the cell surface marker may be used to alter the composition of the preparation such that it displays a higher level of IDO activity as measured by suppression of a T cell proliferation assay (e.g. an allogenic MLR). For example, and referring now to FIG. 4, CD123 enriched ($CD123^+$) APCs may be markedly less efficient at stimulating T-cell proliferation than either the original unfractionated mixture, or the CD123 depleted subset ($CD123^{LO}$) that remains after sorting. In an embodiment, the lack of T-cell activation is due to IDO expression, as shown by the ability of the IDO inhibitor, 1-methyl-(D,L)-tryptophan (1-MT) to prevent suppression.

In an embodiment, a marker associated with $IDO^{LO}$ cells comprises CD14. CD14 (the endotoxin-binding protein receptor) is a well-accepted marker for cells of the monocyte-macrophage lineage (Szabolcs, P., et al., Blood 87: 4520-30 (1996)). Monocyte-derived dendritic cells down-regulate CD14 to undetectable (background) levels when they differentiate along the dendritic cell lineage (Pickl, W. F., et al., *J. Immunol.* 157: 3850-3859 (1996)). Mature myeloid dendritic cells do not express CD14 (K. Shortman and Y.-J. Liu, *Nature Reviews: Immunology* 2: 151-161 (2002)). Thus, in a culture comprising both mature DCs and a second population of non-dendritic APCs expressing CD14, the expression of CD14 can be used to distinguish between the two populations.

For example, as shown in FIG. 3D, adherent cells taken from culture of monocytes in serum-free medium supplemented with GMCSF+IL4 and matured with a cocktail of TNFα, IL1β, IL6 and PGE2 as previously described (Jonuleit, H. et al., *Eur. J. Immunol.*, 27: 3135-3142 (1997)). These cells are not IDO$^+$, but they express markers of APC function (MHC class II, CD80, and CD86) at levels similar to non-adherent (IDO$^+$) cells from the same cultures. Greater than 95% of the IDO$^{LO}$ adherent cells express CD14, whereas less than 10% of the IDO$^{LO}$ adherent cells express CD 123 or CCCR6.

Tolerogenic IDO$^+$ APCs Expressing CCR6 are Recruited to Tumors

Because tolerance-inducing APCs reduce the host's ability to reject foreign antigens which are present on tumor cells, the presence of tolerance-inducing APCs in a tumor is associated with a less favorable prognosis than in cases where tolerance-inducing APCs are not present. As described herein, APCs that have high levels of expression of the intracellular enzyme indoleamine 2,3-dioxygenase (IDO$^+$) express CCR6. CCR6 is a receptor for the chemokine mip-3α, a chemotactic factor for immature dendritic cells (D. Yang, O. M. Howard, Q. Chen, J. J. Oppenheim, *J. Immunol.* 163: 1737-1741 (1999)). Elevated mip-3α expression has been seen in certain tumors (Bell, D., et al., *J. Exp. Med.*, 190: 1417-1426 (1999)).

Embodiments of the present invention recognize that tolerance-inducing APCs that express receptors for chemoattractant factors secreted by the tumors may play a role in the development of tumor-induced tolerance.

For example, malignant melanoma is a tumor with well-defined T cell antigens but which nevertheless is not eliminated by the immune system. In tumor specimens comprising both primary and metastatic lesions, a majority show infiltration of IDO$^+$ cells (FIG. 5B). In a further embodiment, recruitment of IDO$^+$ dendritic cells may also be seen in carcinoma of the breast, lung, colon and pancreas. Accumulation of these cells occurs primarily around the margins of the tumor. Thus, IDO$^+$ APCs may be seen infiltrating along the fibrous stoma, or along the vessels in perivascular cuffs and are not a normal constituent of skin or connective tissue.

Tumor-draining lymph nodes may be a critical site for initiation of anti-tumor immune responses (Ochsenbein, A. F., et al., *Nature* 411: 1058-1064 (2001)). In an analysis of over 300 tumor-draining lymph nodes from 26 patients with malignant melanoma, markedly abnormal accumulation of IDO$^+$ cells is seen (FIGS. 5C-E). The IDO$^+$ cells are found to extensively infiltrate the lymphoid regions of the lymph nodes, largely concentrating in the interfollicular and T cell zones. There is also frequent accumulation around blood vessels (FIG. 5D) and accumulation at the interface between lymphoid tissue and tumor metastases or medullary sinuses (FIG. 5E). Normal lymphoid tissue (tonsillectomy specimens with minimal hypertrophy, or lymph node dissections from patients with early-stage node-negative breast cancer) show only scattered IDO$^+$ cells (FIG. 5F), and do not display the extensive focal collections and confluent areas of IDO$^+$ cells seen in tumor-draining nodes. Also, many primary and metastatic tumors contain individual tumor cells (FIG. 5I) or entire localized regions within the tumor that express mip-3α by immunohistochemistry.

Thus, as shown above (FIG. 5) IDO$^+$ APCs may be recruited to tumors and/or tumor draining lymph nodes. Thus, in an embodiment, the present invention provides methods and compositions to inhibit recruitment of tolerance-inducing APCs to a tumor, tumor draining lymph node or other site of APC recruitment.

Figure 6:
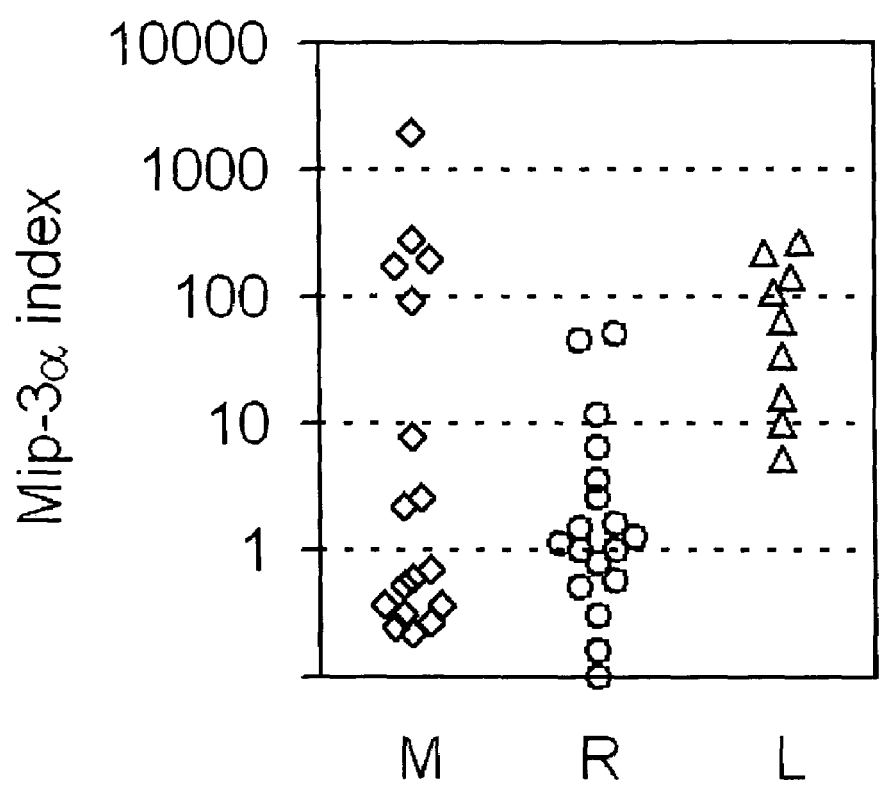
FIG. 6 shows expression of mip-3α mRNA by human tumors in accordance with an embodiment of the present invention. RNA from melanomas (M, n=18), renal cell carcinomas (R, n=19) or non-small cell lung cancers (L, n=9) was analyzed for expression of mip-3α by quantitative PCR calculated as the ratio of mip-3α to the GAPDH housekeeping gene in each sample.

For example, tolerogenic APCs that express CCR6 may be recruited to tumors via mip-3α expressed by the tumor cells. Mip-3α is a known ligand for CCR6, and CCR6 appears to selectively associate with the IDO$^+$ dendritic cell phenotype in vitro. Thus, in an embodiment, mip-3α may be expressed by various tumor cells. For example, as shown in FIG. 6, melanoma, renal carcinoma and lung carcinoma cells comprise increased levels of mip-3α.

Figure 7:
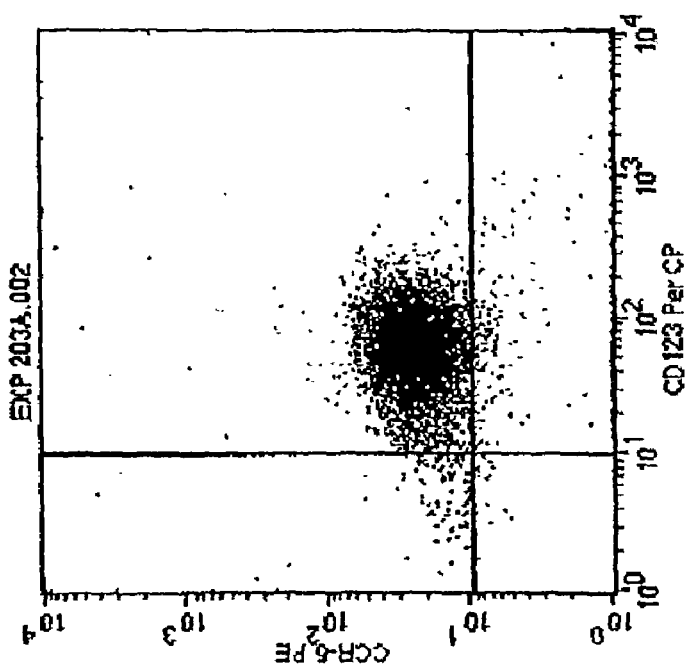
FIG. 7 shows that IDO$^+$/CCR6$^+$ APCs selectively migrate in response to a gradient of mip-3α in accordance with an embodiment of the present invention.
Figure 7:
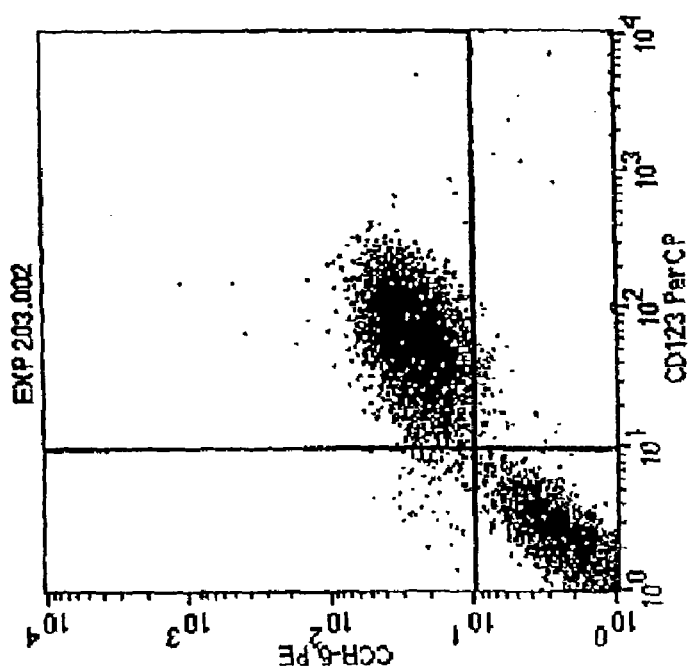

In an embodiment, tumor associated ligands such as mip-3α act to promote migration of tolerance-inducing APCs towards the tumor (FIG. 7). Thus, as shown in FIG. 7 and Table 2 (Example 8, below), CCR6$^+$ IDO$^+$ APCs migrate towards a mip-3α gradient.

Figure 8:
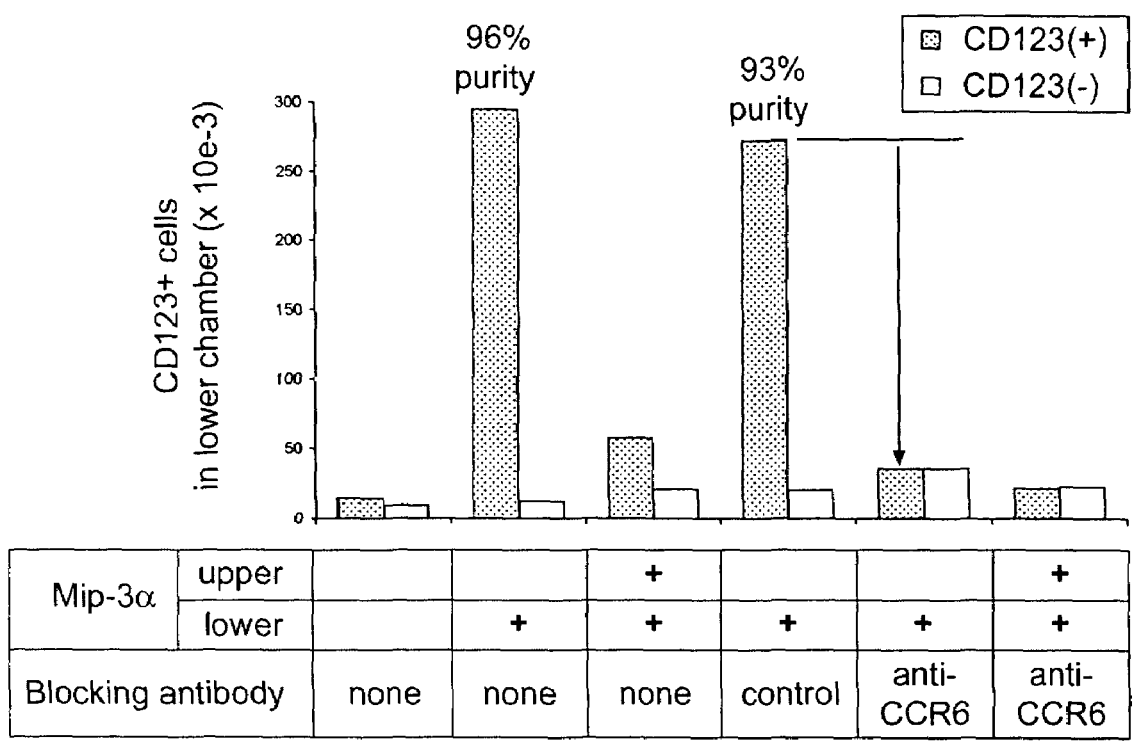
FIG. 8 shows that the migration of IDO$^+$/CCR6$^+$ APCs in response to a gradient of mip-3α is blocked by antibodies to CCR6 in accordance with an embodiment of the present invention.

The present invention provides methods and compositions that inhibit immune tolerance by blocking the interaction of receptors present on the surface of tolerogenic APCs with ligands present at the site of APC recruitment. For example, blocking binding of mip-3α to CCR6 may be used to prevent recruitment of tolerogenic APCs to a tumor. Thus, as shown in FIG. 8, antibodies to CCR6 may be used to block migration of CCR6$^+$ IDO$^+$ APCs towards a mip-3α gradient, such that migration of the APCs from the upper chamber to the lower chamber is inhibited. Compounds that may antagonize or block recruitment of IDO$^+$ APCs to tumors can reduce host tolerance to the tumor. Such compounds comprise, in alternative embodiments, CCR6 antagonists, CCR6 inverse agonists, CCR6 antibodies, and antibodies to mip-3α.

In an embodiment, the high levels of IDO$^+$ cells present in a tumor draining lymph node are associated with reduced survival time. Thus, in an embodiment, the present invention also provides assessing the relative risk of tumor progression by assaying tissue from a tumor or tumor draining lymph node for antigen-presenting cells of myeloid-lineage that are ID$^{O+}$ or have a receptor for a tumor-associated ligand on the surface. In an embodiment, the receptor comprises CCR6. Alternatively, cell surface markers CD 123 and CD11c may be measured.

Generation of IDO+ Cells in Tumor-Draining Lymph Tissue

Lymphoid tissue provides a reservoir for various T-cells involved in the immune response. In addition to draining tumors, lymphoid tissue is involved in developing an immune response during infection.

In some cases, tolerogenic APCs may be involved in preventing the development of an effective immune response to infectious agents. For example, it can be seen in FIG. 9 that IDO$^+$ APCs are detected in HIV-infected lymphoid tissue. Thus, an embodiment of the present invention describes the use of compositions that reduce migration of IDO$^+$ APCs to infected tissue or to lymphoid tissue that is draining the site of infection.

Figure 10:
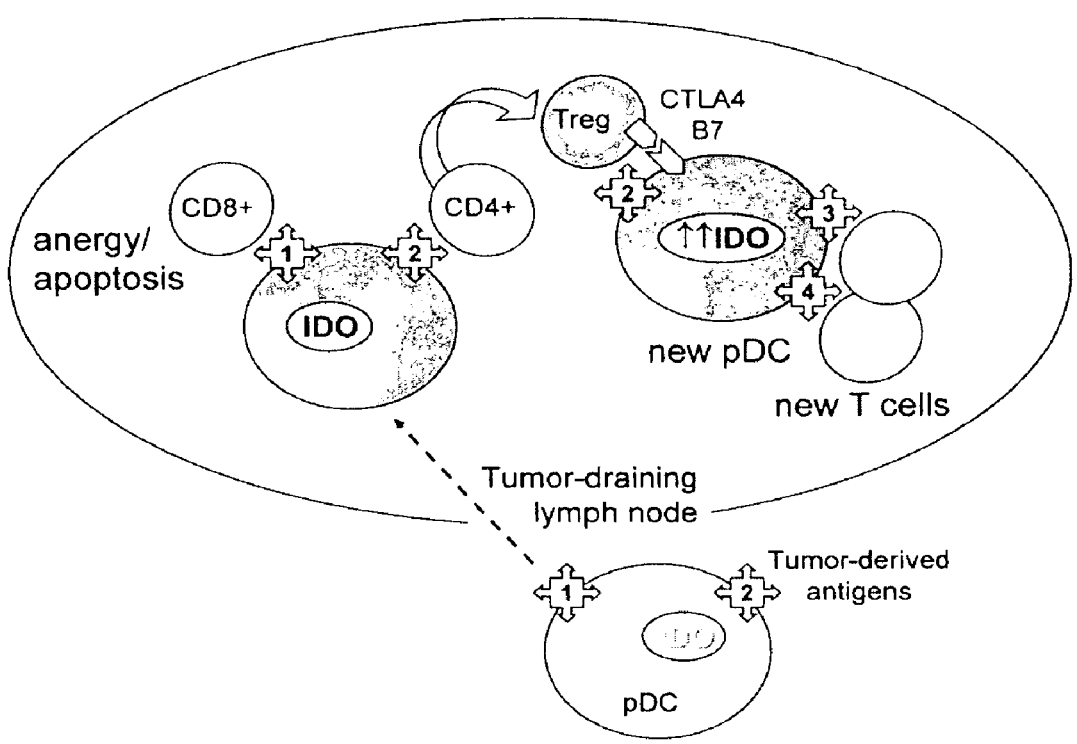
FIG. 10 shows a model for generation of tolerogenic APCs by tumor draining lymph tissue in accordance with an embodiment of the present invention.

FIG. 10 shows a model of how tolerogenic APCs may be generated in lymph tissue. In an embodiment, resting plasmacytoid DCs (pDCs) (a type of APC) that are IDO-competent but not yet expressing IDO migrate from the tumor to the tumor-draining lymph node (LN) bearing tumor-derived antigens. Alternatively, the pDCs may migrate to lymphoid tissue draining a site of infection and/or inflammation.

Once the IDO-competent pDCs are in the tumor-draining LN, they may present antigen to naive T cells and thereby upregulate IDO, perhaps in response to the local cytokine milieu, or to signals from pre-existing regulatory T cells (Tregs). The consequence of this IDO expression may be to directly suppress CD8$^+$ responses, resulting in failure of clonal expansion, anergy and death. Also in an embodiment, Tregs can convert at least some antigen-specific CD4+ T cells into CTLA4+ Tregs. When these Tregs subsequently encounter tumor antigen presented by other, new pDCs (either in the LN, or systemically), they can generate signals via a CTLA4-B7 interaction which may constitutively induce IDO in the new pDCs. The presence of the Treg population may thus be used to render all the pDCs presenting tumor antigen constitutively IDO+.

Figure 11:
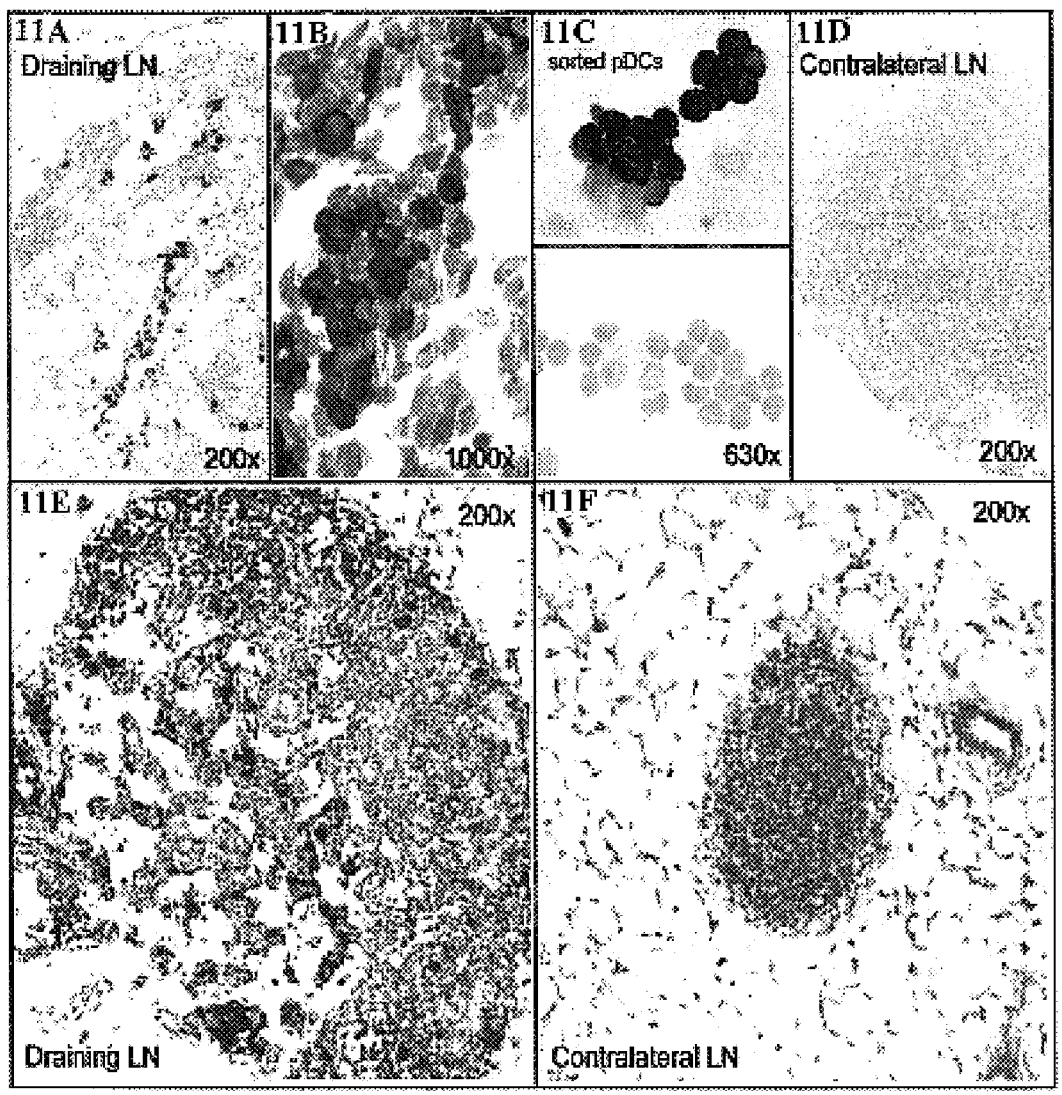
FIG. 11 shows IDO expressing APCs in mouse tumor draining lymph nodes (LN) in accordance with an embodiment of the present invention. Shown are: (A) draining inguinal LN from a mouse with a B16F10 tumor (IDO in red chromogen) and (B) a high-power view of the specimen in panel A. Panel (C) shows a tumor-draining LN, as in panel A, sorted into the B220$^+$CD11c$^+$ population (upper panel) versus all other cells (lower panel); cytospins of each fraction are shown stained for IDO (DAB chromogen, brown). Panel (D) shows a contralateral LN from the animal in panel A, stained for IDO (red), demonstrating absence of IDO$^+$ cells; staining controls (the anti-IDO primary antibody neutralized with a molar excess of the immunizing peptide) looked identical to panel D, and these data are not shown. Panel (E) shows draining LN from B78H1/GMCSF-transfected tumor (day 12, viable established tumor, not irradiated), stained for IDO (red); and (F) shows the contralateral LN from the same animal as in panel E, stained for IDO.

For example, in some cases there is significant accumulation of IDO+ cells in the tumor draining lymph node that are not present in a contralateral (non-tumor draining) lymph node (FIG. 11). Thus, as shown in FIG. 11, IDO+ (B220+ CD11c+) cells are selectively found in the tumor draining lymph nodes of mice with a B16F10 melanoma tumor (FIGS. 11A, 11B, and 11C), but are not found in the contralateral lymph node (FIG. 11D).

Figure 12:
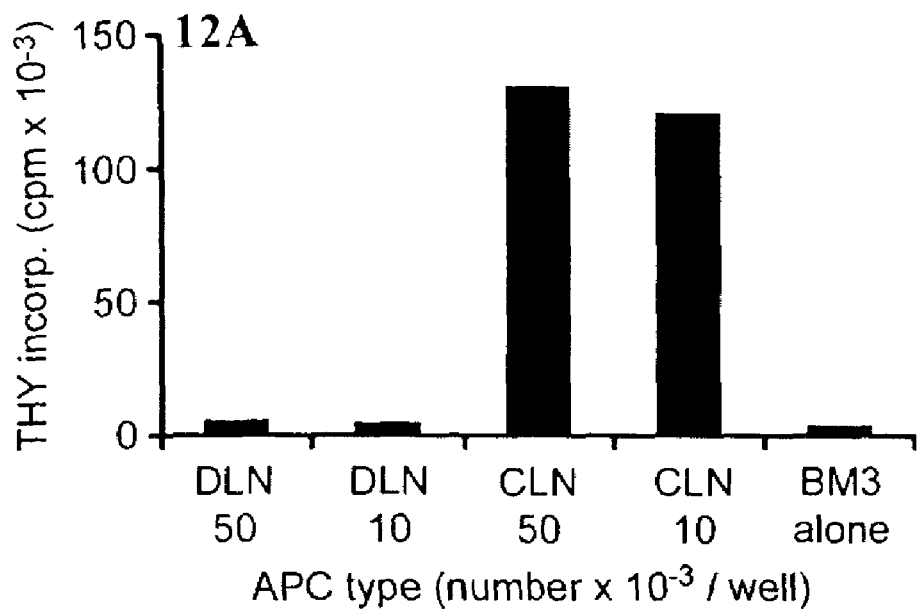
FIG. 12 shows suppression of T cell responses by tumor-draining LN cells in accordance with an embodiment of the present invention. Cells from tumor-draining LN (DLN) and contralateral LNs (CLN) were harvested from mice with B78.GM tumors (day 14), and used as stimulators in MLRs. Responder cells were TCR-transgenic BM3 cells. The number of stimulator cells is shown for each group (the number of responder cells was fixed at 50,000 nylon-wool purified BM3 T cells). Panel (A) shows conventional MLR, indicating a profound defect in response when stimulators were from the DLN. Response with CLN stimulators was comparable to stimulators from non-tumor-bearing mice (not shown). Panel (B) shows mixing experiments (DLN+CLN) indicating that the defect in response was due to a dominant suppressor activity present in the DLN cells. (All groups received 50,000 BM3 responders). The day 14 draining LNs did not contain any detectable tumor metastases at the time of analysis, indicating that the suppressive effects were mediated by host cells.
Figure 12:
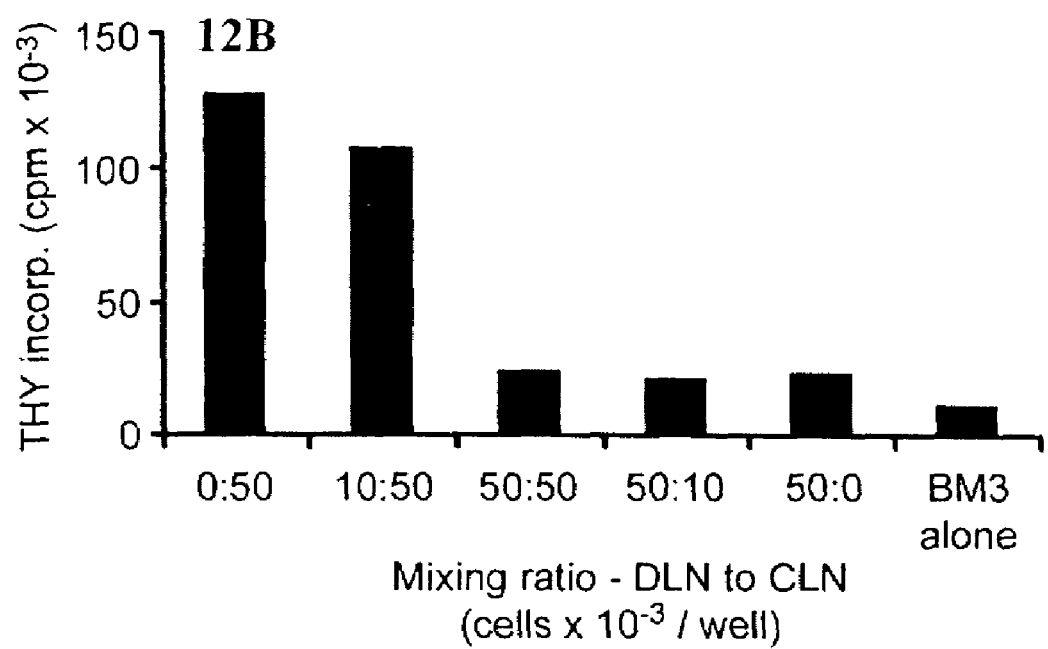

Also, in an embodiment, at least one population of the cells are tolerance-inducing. For example, FIG. 12A illustrates the inability of cells isolated from the tumor draining lymph node to activate a T cell response (MLR). The tolerogenic nature of these cells is due at least in part to increased levels of IDO as shown by the ability of 1-MT to reverse the effect (not shown). Interestingly, in an embodiment, the tolerance-inducing effect is dominant. Thus, as shown in FIG. 12B, mixing IDO+ tolerance-inducing cells with non-tolerance inducing cells results in inhibition of the T cell response as measured by the MLR assay.

Figure 13:
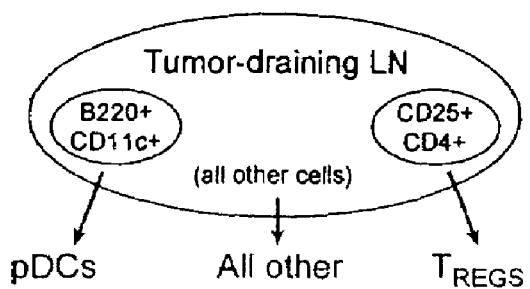
FIG. 13 shows that both regulatory APCs (APCregs) and regulatory T cells Tregs are present in tumor-draining lymph nodes in accordance with an embodiment of the present invention. Panel (A) shows tumor-draining LN cells from a wild-type (IDO-sufficient) C57BL/6 host. The arrows indicate the IDO-mediated (1MT-sensitive) component of inhibition. Panel (B) shows tumor-draining LN cells from an IDO-knockout host, showing no IDO-mediated inhibition (but with inhibition by Tregs intact).
Figure 13:
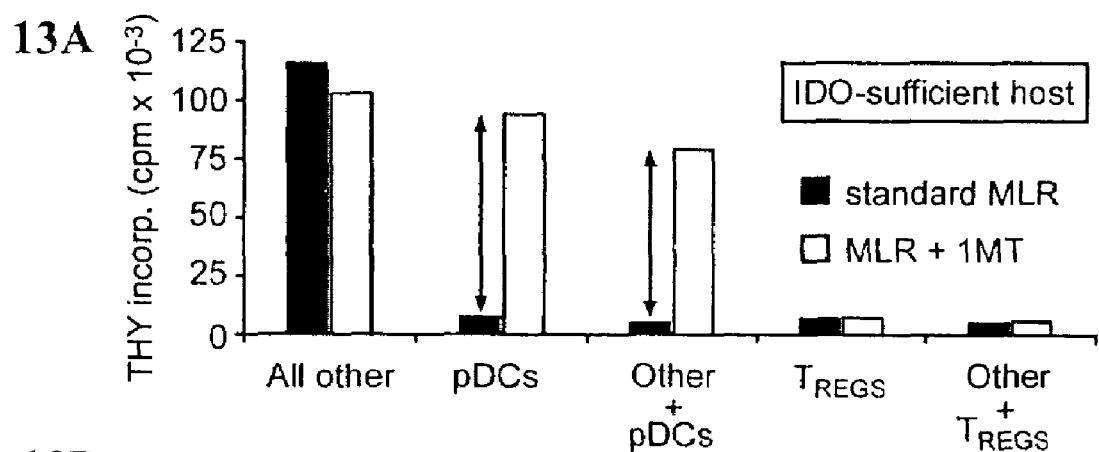
Figure 13:
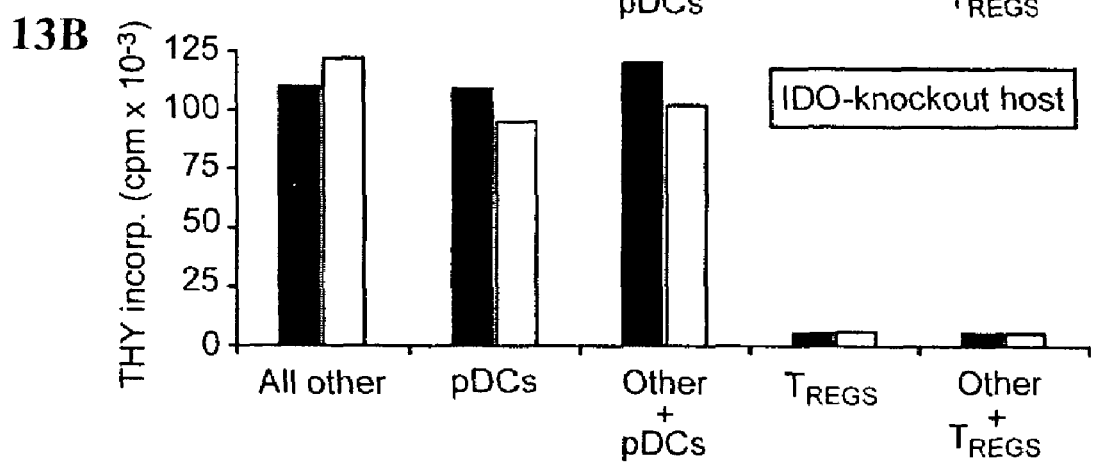

Also, in an embodiment, cells isolated from tumor-draining lymph nodes may comprise several populations of cells, wherein each population comprises different levels of tolerance-inducing ability (FIG. 13). Thus, in an embodiment, tumor draining cells may comprise at least the following fractions: (1) a B220+ CD11c+ plasmacytoid dendritic cell (pDC) fraction; (2) a CD25+ CD4+ regulatory T-cell (Treg) fraction; and (3) a third "all other" fraction. In an embodiment, the "all other" fraction of cells stimulates T cell proliferation, with no enhancement of the stimulation by 1MT, indicating that there is little to no IDO-mediated suppression present in the "all other" fraction. In contrast, the B220+ CD11c+ (pDC) fraction may be potently inhibitory (FIG. 13A); that this is IDO mediated inhibition (rather than simply a lack of antigen-presenting ability) is demonstrated by the fact that suppression was fully reversed by adding 1MT. Mixing experiments (i.e., B220+ CD11c+ pDCs plus the "all other" fraction) showed that IDO-mediated suppression may be dominant, and can be fully reversed by adding 1MT. This result indicates that the only difference between an inhibitory pDC and a stimulatory pDC is whether or not IDO is active. Thus, IDO is not merely "associated" with the suppressive pDC phenotype—it is the direct causative mechanism of suppression by these cells. The CD25+ CD4+ (Treg) fraction also showed inhibition (which was also dominant in mixing experiments). However, the suppression mediated by Tregs was not affected by 1MT, as Tregs do not express IDO.

Thus, in an embodiment, the tumor-draining LNs contain two suppressor activities: (1) the direct suppression mediated by IDO+ pDCs, and (2) an IDO-independent component of suppression mediated by Tregs. This finding of regulatory pDCs and regulatory T cells together in the tumor-draining LN is consistent with the model proposed in FIG. 10. Also, where the tumor draining lymph nodes are taken from an IDO-knockout host (FIG. 13B), inhibition by the pDC fraction is completely absent (i.e., there is no suppression when pDCs were mixed with the "all other" group. There was also no enhancing effect of 1MT in any group, confirming the lack of IDO expression.

Development of CCR6 Antagonists

A. Determination of the CCR6 Antagonist Ability to Inhibit Migration of IDO+ APCs In an embodiment, the present invention comprises a methods to determine the ability of candidates to block chemotaxis and microinvasion induced by mip-3α and/or other ligands.

For example, in an embodiment, chemotaxis experiments are performed using a Boyden chamber to measure "chemoinvasion" which reflects invasive behavior. For example, in these assays, a mixture of $IDO^{LO}$ APCs ($CCR6^{LO}$) and IDO+ APCs (CCR6+) may be placed in Boyden chambers and chemoattractant stimuli are placed in the lower wells, which are separated by a polycarbonate membrane coated with fibronectin. Antagonists may then be added in the upper chamber with the APCs and the chemotactic response measured after 4 hours incubation at 37° C. by measuring IDO+ APCs or CCR6 on the lower aspect of the membrane. Cells penetrating the polycarbonate membrane to the lower aspect are counted in four high power fields in at least two chambers.

B. Functional Expression of CCR6 in *Saccaromyces Cerevisiae*

In an further embodiment of the present invention, an analysis of mutations in the CCR6 gene, or the genes for other receptors specific to IDO+ cells, is undertaken as a means to develop agents that block binding of the receptor to its ligands.

For example, CCR6 can be functionally expressed in *S. cerevisiae* for the purpose of screening putative antagonists and for generating constitutively active mutants (CAMs). Similar studies have been performed by the inventors using related cytokine receptors CXCR4 and CCR5. Thus, chemokine receptors CXCR4 and CCR5 were expressed in a yeast strain in which these guanine nucleotide protein receptors (GPRs) were coupled to the mating pheromone response pathway by a mammalian/yeast hybrid G subunit. Consequently, stimulation of CXCR4 and CCR5 by the cognate ligands (SDF-1 and RANTES, respectively) activated signal transduction that results in histidine prototrophy or, in strains also carrying a pheromone-responsive FUS1-lacZ reporter gene, beta-galactosidase expression. In these experiments, SDF-1 stimulated histidine-independent growth and reporter gene expression in yeast strains expressing CXCR4-WT, but not in control cells lacking the receptor. A CXCR4 variant with an N-terminal epitope tag and a C-terminal hexa-histidine (6xHis) motif, which was prepared for structure-function studies, demonstrated a response to SDF-1 that was identical to that observed with the CXCR4-WT. All available CXCR4 antagonists blocked growth in histidine deficient medium resulting from CXCR4 activation and the induction of reporter gene expression stimulated by SDF-1. Thus, it was found that upon successful transfection into yeast of CXCR4 or CCR5 subcloned in the Cp4258 vector, ligands for CXCR4 or CCR5 stimulate histidine independent growth (and reporter gene expression), and antagonists inhibit the stimulation.

Thus, in an embodiment of the present invention, CCR6 may be expressed as a fusion protein with the alpha-factor mating pheromone signal peptide to insure proper cellular trafficking. Since a panel of immunologic reagents to CCR6 are currently not available, Myc and 6xHis epitope tags may be inserted at the amino- and carboxy-terminus, respectively, to confirm receptor expression in yeast cell transformants. These CCR6 expressing cells may then be used to screen libraries of putatitve antagonists for compounds that alter mip-3α induced, histidine-independent, growth.

Once transformants having mip-3α inducible (i.e. CCR6-dependent) signaling are isolated, random mutagenesis may be performed using techniques known in the art to generate constitutively active mutants. To isolate CCR6 CAMs, mutants that have autonomous expression of the FUS1-HIS3 reporter gene, CAMs may be selected for the ability to grow in medium lacking histidine (i.e. without the addition of mip-3α ligand). Once CCR6-CAMs are available, libraries of putative antagonists may be screened to identify compounds that alter the histidine-independent growth conferred by the CCR6-CAM.

Also, CCR6 CAMs may be sequenced to determine the nature of the mutations that confer constitutive activity. Once residues that are important for activity are identified, they may be further investigated. For example, for CXCR4, conversion of one particular residue was common to several CXCR4 CAMs. This was confirmed by site-directed mutagenesis, in which mutation of the CAM back to wild-type at this residue restored normal function. Subsequent saturation mutagenesis of the identified residue indicated that conversion of the identified residue to selected amino acids conferred transformants that lacked signal transduction in the presence or absence of ligand stimulation. Similar types of analyses may be performed for CCR6.

Also, alanine scanning mutants (in which each residue is systematically replaced with alanine) may be developed and tested to determine residues in CCR6 that are required (or not required) for function. The inventors have done similar analyses using CXCR4 and determined that four out of 84 scanning mutants are not blocked by antagonists, indicating that at least these four residues are important for activity.

The mutants may also be analyzed for proper cell trafficking. For example, the inventors have performed similar analyses for CXCR4, where it was determined that the expression of CXCR4-WT (the wild-type transfected into yeast) was similar to that of two constitutively active mutants. In contrast, a third CAM displayed lower expression despite similar biological activity (once expressed).

For CXCR4, there appeared to be no differences in the steady state levels of the CXCR4 variants. Still, the possibility that there was variation in trafficking to the cell membrane was evaluated. Since such experiments are difficult to perform in yeast, the open reading frames encoding the CXCR4 variants were subcloned into pcDNA3 and trafficking to the cell surface was determined by flow cytometric analysis of QT6 transfectants. All of the CXCR4-CAMs and variants lacking the activating mutation showed significant expression on the cell surface. These findings indicated that the biological activities observed for the CXCR4 variants was not the result in differences in expression or intracellular trafficking.

Compounds may also be tested for their ability to act as inverse agonists. Inverse agonists act by blocking expression of the receptor, rather than by competitively inhibiting binding of an agonist ligand to the receptor. For example, four antagonists of CXCR4-WT were tested for effects on the autonomous signaling of one of the constitutive mutants. Two antagonists increased activity of the mutant, whereas a third antagonist dramatically decreased the autonomous signaling of one CAM. These findings indicate that the first and second antagonists are CXCR4-WT antagonists that increase the signaling of CXCR4-CAM and that the third antagonist is an inverse agonist and thus decreases autonomous activation of the pheromone response pathway.

C. Libraries

In a further embodiment, molecular biology is combined with computational modeling to develop a structural rationalization for the binding of chemokine receptor antagonists to their receptors. Several libraries may be screened for compounds that are CCR6 antagonists. Such libraries include, but are not limited to: (1) commercially available libraries of compounds available from biopharmaceutical companies, and in particular, protein/peptide libraries; (2) combinatorial libraries of compounds, and in particular, protein/peptide libraries; and (3) libraries of mip-3α mutants. In addition, monoclonal antibodies to CCR6 and mip-3α may be screened for antagonist activity.

For example, candidate pentapeptides can be identified through screening of a combinatorial library of cyclic peptide and pseudopeptides libraries. (A. F. Spatola and Y. Crozet, J. Med. Chem., 39: 3842 (1996)). These libraries were generated primarily using medium sized head-to-tail cyclic peptides (5-8 amino acids), as they approximate "reactitopes" and are mimics of structures involved in ligand-receptor interactions. By using side chain attachment of the initial amino acid, followed by elongation and on-resin cyclization, either individual cyclic peptides or mixtures can be obtained.

Additionally, any of the above protein or peptide libraries can be resynthesized with additional amino acid replacements. For example D,L-Lys can replace D,L-Arg and a portion of a ring that is less likely involved as a pharmacophore (such as a Pro-Pro fragment) can be replaced with a turn mimic or stabilized non-peptide replacement such as 3-aminomethylbenzoic acid.

D. Analysis of the Biologic Activity of Putative CCR6 Antagonists in Mammalian Cells In a further embodiment, the biologic activity of putative antagonists for CCR6, or other cell surface proteins specific to IDO+ APCs, is assessed in mammalian cells. Thus, the activity of putative CCR6 antagonists may be first assessed in vitro using the chemotaxis assay and the yeast system described herein, and a putative dose-response relationship determined. Promising compounds may then screened in the yeast signaling system for the ability to alter the activity of CCR6-CAM mutants, where inverse agonists decrease activity and antagonists increase activity. Agents that have significant activity in altering the activity of CAMs or in chemotaxis assays may then be tested for the ability to block the activation of CCR6-WT by mip-3α in yeast strains.

Compounds with significant activity in the yeast system may be selected for testing as CCR6 antagonists in mammalian cells. Thus, for those compounds that demonstrate antagonist/inverse agonist activity in yeast, characterization of the efficacy in mammalian cells may be undertaken with experiments to assess: (1) displacement of mip-3α binding; (2) inhibition of calcium mobilization by mip-3α (3) antagonism of mip-3α-induced γ[$^{35}$S]GTP binding; and (4) blocking decreased forskolin-induced accumulation of cAMP. For example, CHO CCR6 transfectants may be used to test the ability of active compounds to block the binding of radiolabeled mip-3α using standard techniques such as Scatchard analysis of radioligand binding. Compounds that demonstrate significant displacement of binding may then be further tested for the ability to block CCR6 signaling in response to mip-3α using calcium flux experiments with CHO CCR6 transfectants loaded with Fura2. Signaling will also be determined in a gamma [$^{35}$S]GTP binding assay in which membrane fractions from CCR6 transfectants are incubated with this non-cleavable GTP analog in the presence and absence of mip-3α.

E. Dissection of the Molecular Anatomy of CCR6 Antagonists

Once a positive lead compound is identified, it can be systematically modified, as for example, by performing an alanine scan (replacing each residue with either D- or L-alanine) to establish the critical binding sites. The inventors have performed similar studies with CXCR4 and have identified five alanine scanning mutations of a selected antagonist that prevent antagonism of CXCR4. Once the critical sites on the antagonist are identified, the non-contributing fragments may be substituted with new functional groups (e.g., Thr, His, Trp, NaI, etc.) in order to enhance binding, selectivity, and/or bioavailability. Structurally optimized candidates are further modified, such as by adding poly(ethylene glycol) bioconjugates or equivalent groupings, to assist in delivery considerations.

Once the inhibitory activities observed in yeast are confirmed in mammalian cells, and the critical sites for antagonist function are identified, the structure of the putative antagonist may then be determined (e.g., by NMR spectroscopy for cyclic peptides and other constrained molecules) and an identification of the residues required for inhibitory activity may be undertaken. Also, antagonists may be evaluated by their ability to prevent tumor formation in vivo.

F. Determination of the Role of CCR6 in the Metastatic Behavior of Tumor Cells in vivo In a further embodiment of the present invention, the effect of CCR6 antagonists on the metastatic spread of melanoma may be determined using xenotransplantation of mip-3α expressing B16F10 mouse melanoma tumor cells into severe combined immunodeficient (SCID) mice. Similar approaches have been used to elucidate the activities of other chemokine receptors (and antagonists thereof) in the development of tumors.

For example, the MDA-MB-231 cell line is derived from a human mammary carcinoma and has been shown to spontaneously metastasize to the lung following orthotopic injection into the mammary fat pad and to form lung metastases after intravenous injection (Muller, A., et al,. Nature, 410: 50-56 (2001)). This human breast cancer cell line expresses the chemokine receptor, CXCR4, and exhibits a chemotactic response to the CXCR4 ligand, SDF-1. It has been found that the metastatic behavior of MDA-MB-231 cells is diminished by monoclonal antibodies to CXCR4.

Thus, in these experiments, putative CCR6 antagonists may be administered prior to implantation of mip-3α expressing B16F10 cells in order to optimize the effect that is observed. For example, an antagonist to the CXCR4 receptor has been administered to mice by intraperitoneal injections of 2 mg per day without evidence of toxicity. Also injection of 25 µg per day vMIP-II, a high affinity chemokine antagonist that appears to recognize several chemokine receptors, also does not have adverse effects (see e.g., Chen, S., et al., J. Exp. Med., 188: 193 (1998)).

Mice given daily injections of either CCR6 antibodies, CCR6 anatgonists, or control buffer, are assessed for inhibition of the metastatic behavior of the tumors at various time periods (e.g., 28-60 d) (Muller, et al., Nature, 410: 50-56 (2001)). Micro-metastases are counted and the relative infiltration by tumor cells quantitated.

G. Rational Design of Second Generation CCR6 Antagonists

In a further embodiment, the present invention comprises the development of second generation antagonists based upon the structure of known antagonists. The rational design of second generation antagonists is enhanced by determining the structure of known antagonists. For example, the inventors have determined the structure of a specific CXCR4 antagonist, by NMR and subsequently used that to determine plausible models that explain available biological data, such as critical residues required for activity.

i. Determination of the Cyclic Peptide Structures by NMR

The calculated structures of some first generation antagonists (e.g. cyclic peptides and other conformationally restricted molecules) may initially be determined by NMR using a 600 MHz NMR spectrometer. For example, although linear pentapeptides typically have no persistent structure, cyclization greatly reduces the degrees of freedom accessible to the peptide backbone, so that there is usually a closely related family of preferred conformations, especially when an included residue is proline whose f value is restricted in a narrow range of Ramachandran space. Thus, the structures of the initial hits from the yeast screen of such cyclic peptides can be determined by NMR. The resonance assignments of the peptides may be made in aqueous solution, typically in phosphate buffer at neutral or slightly acidic pH. Residue types are identified using TOCSY with Watergate for solvent suppression (A. Bax and D. G. Davis, J. Magn. Reson., 65: 355-360, (1985)). Any ambiguities remaining in the sequence-specific assignments after the initial analysis may be resolved using ROESY experiments, which are superior to NOESY for molecules of this size (D. Neuhaus & M. P. Williamson, The Nuclear Overhauser Effect in Structural and Conformational Analysis, VCH New York (1989)). The ROEs obtained at different mixing times supply essential distance restraint data for solving the structures of the molecules. These data can be augmented with torsion restraint information derived from three-bond scalar coupling information, especially $^3J_{NH\alpha H}$ and $^3J_{\alpha H\beta H}$. Additional conformational information can be extracted from $^{13}C$ chemical shifts (Wishart, D. S., et al., J. Biomol. NMR, 6: 135 (1995)); Comilescu, G., et al., J. Biomol. NMR, 13: 289 (1999)) which can be obtained in a straightforward fashion for small peptides at >1 mM using HSQC (G. Bodenhausen and D. J. Ruben, Chem. Phys. Lett., 69: 185 (1980)). Depending on the nature of the side-chains, they may be dynamically disordered, which may require care in interpreting the ensemble-averaged NMR data. Resolution of this problem may be achieved in conjunction with molecular dynamics simulations in water, and comparing the expected time trajectory-averaged properties with the experimental data (Piotto, M., et al., J. Biomol. Str., 2: 661-665, (1992)). Conformational interchange between two or more states is sometimes observed in restricted peptides. These can be characterized by recording spectra at different temperatures and examining relative populations as a function of temperature and from the sign and magnitude of ROESY cross-peaks if the time scale is appropriate.

Similar studies have been performed by the inventors for CXCR4 antagonists. A detailed NMR investigation of the conformation of a specific antagonist peptide under physiological conditions was performed and essentially complete $^1H$, $^{13}C$ and $^{15}N$ (at natural abundance) assignments obtained using a variety of homo- and heteronuclear 2D NMR experiments to define the structure primarily at the backbone level.

ii. Optimizing Combinatorial Libraries

A number of structural variants can be systematically incorporated into the initial cyclic peptide antagonists to improve further the potency and selectivity. Table 1 contains a list of the common side chain constraints and their most notable characteristics. For example, N-methylation reduces H-bonding and increases organic solubility as does alpha-methylation of amino acids. Modifications using the functional groups described herein commonly are associated with improvements in potency of at least 2-3 orders of magnitude, along with commensurate selectivity gains.

Additional second generation changes may also focus on the amide linkages in the molecule, which represent potential problem areas with bioavailability in general. By replacing one or more of the peptide bonds, either with a suitable beta-turn mimic or by an amide bond surrogate (A. F. Spatola, in "Chemistry and Biochemistry of Amino Acids, Peptides, and Proteins", ed. B. Weinstein, Marcel Dekker, New York, Vol. VII, pp. 267, (1983)) these analogs should be rendered more suitable for further structure activity studies, physico-chemical characterization, and for further biological evaluations using in vivo systems.

TABLE 1

Peptide conformational constraints and their characteristics

| | Modification | Effect | Example |
|---|---|---|---|
| 1 | D-amino acid | Altered orientation, turn stabilization | D-Arg, D-Nal |
| 2 | N-Methylation | Reduces hydration sphere; increases lipophilicity | N-MePhe |
| 3 | α-Methylation | Steric buttressing, reduced degrees of freedom, reduction in $\phi$, $\psi$ angle mobility | Aib, Deg |
| 4 | β-Methylation | Effect on χ-space; locks in side chain orientation | β-MeTyr |
| 5 | Disulfide formation | Potential bicyclic formation and further reduction in entropic penalty | Cys-Cys, Pen-Pen |
| 6 | β-turn mimics | Locks in position of turn and reduces ring mobility | Pro-D-NMe-Ala; heterocyclic mimics | iii. Rational Design Using Combinatorial Libraries

As described herein, peptides isolated from combinatorial libraries provide initial molecules that can be enhanced by determining their structures and using structure-based rational drug design. Most effective drugs in the clinic are not natural peptides, but are natural product derivatives or synthetic molecules. Thus, it may be necessary to further develop the cyclic peptides to produce effective second generation inhibitors.

Cyclic peptides provide a scaffold that allows for rational drug design using at least two computational approaches used for the pharmacophore development. One approach is to screen libraries of three-dimensional structures of known and available compounds against the newly identified pharmacophore. For example, the NIH structure database and the Available Chemicals Database, containing 247,000 and 500,000 structures, respectively, may be screened using Tripos software FlexS and Unity. A second approach is an enhancement of virtual screening, where using for example, COMBICHEM software, a virtual library is generated using the cyclic peptide as a scaffold but replacing the side chains with synthetically available moieties. These libraries can provide greater than 500,000 new molecules that can be used for further refinement. In both cases the new "hits" are synthesized and tested using the yeast assay to identify new lead compounds that do not have the disadvantages of using a cyclic peptide.

iv. Development of a Structure-Activity Relationship Based on Biomolecular Interactions with CCR6

In an embodiment, mechanistic and dynamic information are used for the rational design of inhibitors. Mechanistic and dynamic information may provided by: (1) fully solvated lipid bilayer simulations of a CCR6-CAM; (2) simulations to elucidate the structural mechanism using mutations of residues known to be active in binding or biological activity; and (3) docked structures of putative cyclic peptide antagonists complexed with CCR6. This information is then used for the rational design of enhanced inhibitors.

The ability to examine the inhibitor-CCR6 complex may provide insights into the biomolecular interactions and induced conformational change associated with binding. The inventors have previously used molecular modeling calculations combined with molecular biology to produce a model of CXCR4 that is consistent with structural and experimental data. The dynamic signaling mechanism of CCR6 may be elucidated by examining the effect of chemokine binding to the receptor. The CCR6 constitutively active mutants can be employed explore multiple structural changes that associated with these mutants.

Lead compounds may be docked into the CCR6 structure using similar protocols as for CXCR4 and its known antagonist, T140, and simulations run on the complexes. This type of analysis may provide additional information for the structure-activity relationship and refinement of the pharmacophore that is otherwise unobtainable. This, combined with the identification of critical residues associated with binding each lead compound, may enable generation of a detailed map of biomolecular interactions, which in turn can be used for rational design to further optimize these compounds for activity and specificity.

For example, homology models of CXCR4 have been generated using Modeler (A. Sali & T. L. Blundell, *J. Mol. Biol.*, 212: 403 (1990)) with an alignment (Omiga) of the bovine rhodopsin sequence and high resolution X-ray structure (Palczewski, K., et al., *Science* 289: 739 (2000), see also Comment in: *Science*, 289:733-4 (2000)). The initial approach used state-of-the-art molecular dynamics simulations to relax the extracellular regions of CXCR4. Intially, the NMR structure of a specific CXCR4 antagonist under physiologic conditions was determined, and used in the antagonist-CXCR4 simulation. The antagonist was placed in two orientations with the experimentally determined critical residues located close in space to those identified by the molecular biology inhibitor studies by docking. After 300 ps of equilibrium of the solvent/protein system, a 3.5 nanosecond production phase molecular dynamics simulation was obtained. One model had direct H-bonding interactions with two critical residues in CXCR4 identified by the fusion assay.

Therapeutics

The invention contemplates methods of administration which are well known in the art. For example, in an embodiment, administration of the compound is systemic, as for example by parenteral administration, using intramuscular, subcutaneous, intravenous, or intra-arterial routes. In yet another embodiment, administration is topical. In another embodiment, the method of administration is by a transdermal patch. Also, administration may employ a time-release capsule. In yet another embodiment, administration of the compound is oral or as an aerosol. In another embodiment, administration of the compound is sublingual.

Pharmaceutical formulations can be prepared by procedures known in the art. For example, the compounds can be formulated with common excipients, diluents, or carriers, and formed into tablets, capsules, suspensions, powders, and the like. Examples of diluents that are suitable for systemic administration include water, saline and/or buffered physiological solutions. Also, physiological preservatives (e.g., benzalkonium chloride), antibiotics, and compounds to adjust the osmolarity of the formulation of the solution may be included.

Other fillers and carriers which may also be employed, depending upon the method of uptake, include the following: fillers and extenders such as starch, sugars, mannitol, and silicic derivates; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

In an embodiment, the dose of the composition administered comprises levels of the therapeutic agent of interest (i.e., CCR6 antagonist) that may be used pharmacologically in animals and humans. Also preferably, the dose of agonist results in a concentration at the receptor which ranges from 0.005 nM to 50 µM, and more preferably, from 0.05 nM to 1 µM, or even more preferably, from 1 nM to 100 nM.

Also, the ability of chemokine antagonist to bind to its receptor may a function of cell division and the length of the cell cycle. Thus, application of the compound comprising an antagonist (or other compound able to interact with proteins on tolerance inducing APCs such as an antibody) may be hourly, daily, or over the course of weeks. Thus, preferably, the effective amount of the antagonist/antibody comprises from about 1 ng/kg body weight to about 200 mg/kg body weight. More preferably, the effective amount of the antagonist/antibody comprises from about 1 µg/kg body weight to about 50 mg/kg body weight. Even more preferably, the effective amount of the antagonist/antibody comprises from about 10 µg/kg body weight to about 10 mg/kg body weight. Alternatively, a continuous level of antagonist/antibody ranging from about 0.05-10,000 µg/kg/hour, or more preferably, 0.5-250 µg/kg/hr, or even more preferably 5-50 µg/kg/hour may be employed. The actual effective amount will be established by dose/response assays using methods standard in the art. Thus, as is known to those in the art, the effective amount will depend on bioavailability, bioactivity, and biodegradability of the compound.

EXAMPLES

Example 1

Cell Culture

Human monocytes and lymphocytes were isolated by leukocytapheresis and counterflow elutriation (D. H. Munn et al., *J. Exp. Med.* 189, 1363-1372 (1999)). Monocytes (typically >95% purity) were cultured in 100 mm tissue culture petri dishes in RPMI-1640 medium with 10% newborn calf serum (Hyclone) and including penicillin/streptomycin and glutamine. Cultures received either MCSF (200 U/ml, Genetics Institute) on day 0, or GMCSF (50 ng/ml, R&D Systems)+ IL4 (50 ng/ml, R&D Systems) on days 0, 2 and 4. For experiments where CCR6 expression was of interest, cultures received a single dose of GMCSF+IL4 (100 ng/ml each) on day 0, with no further supplementation. Loosely adherent dendritic cells (GMCSF+IL4) were harvested by gentle aspiration; adherent macrophages (MCSF) and non-dendritic APCs (GMCSF+IL4) were harvested with EDTA. Other cultures were conducted in serum-free medium (X-vivo 15; Bio-Whitaker, Walkersville, Md.) plus cytokines.

Example 2

Production of Antibodies

All antibodies were obtained commercially except for polyclonal antiserum against human IDO which was manufactured as a work for hire by ZCB Inc., Hopkinton, Mass. All commercial antibodies and reagents were from BD Biosciences-Pharmingen (San Jose, Calif.) unless specified otherwise. For detection of cell surface antigens, DCs were triple-stained with anti-CD123-biotin (clone 7G3; it was found that clone 9F5 gave suboptimal results with dendritic cells) followed by streptavidin-perCP, plus anti-CD11c-allophycocyanin (clone S-HCL-3) or anti-CCR6-fluorescein (clone 53103.111, R&D systems, Minneapolis, Minn.). CCR6 results were also confirmed using a second anti-CCR6 antibody (clone 11A9; Pharmingen). For detection of IDO, cells were fixed and permeablized (Cytofix/Cytoperm), and then stained with rabbit anti-IDO antibody prepared against the peptide followed by polyerythrin-labeled anti-rabbit secondary antibody (Jackson Immunoresearch, West Grove Pa.) cross-adsorbed against mouse, human and bovine IgG, for multiple labeling). Dendritic cells were gated on forward and side scatter to exclude contaminating lymphocytes and debris.

For preparation of rabbit anti-IDO antibody, the peptide DLIESGQLRERVEKLNML ( SEQ ID NO: 1) corresponding to residues 48-67 of human IDO (GenBank sequence M34455) was prepared and conjugated by addition of a terminal cysteine to keyhole limpet cyanogen. Rabbits were immunized with conjugated peptide in Freund's adjuvant (all immunization, antibody preparation and affinity purification steps were performed as a work for hire (QCB, Inc., Hopkinton, Mass.)). This peptide gave the best results out of several different sequences screened for their ability to detect human IDO in formalin-fixed paraffin-embedded tissue and by flow cytometry. Validation studies showed that this antibody immunoprecipitated the expected 45 kD band from cell lysates, correlated with IDO mRNA and functional enzymatic activity in vitro, identified an interferon-γ-inducible antigen in two known-positive cell lines (THP-1 and HeLa), and detected an antigen by immunohistochemistry which was specifically localized to cells with known expression of IDO (the syncytiotrophoblast cells of human placenta; Y. Kudo and C. A. Boyd, *Biochem. Biophys. Acta* 1500, 119-124 (2000)). Results were consistent from animal to animal, and from lot to lot of antibody.

Example 3

Co-Expression of IDO with Cell Surface Markers CCR6, CD123, and CC11c in APCs

Expression of IDO in immature monocyte-derived (myeloid) dendritic cells (Dhodapkar, M. V., et al., *J. Exp. Med.* 193: 233-238 (2001)) and in immunosuppressive monocyte-derived macrophages (Munn, D. H., et al., *J. Exp. Med.* 189: 1363-1372 (1999)) was analyzed. FIG. 3 shows the expression of IDO and CCR6 by myeloid antigen-presenting cells which express the cell surface antigen CD123 (CD123$^+$). Human monocytes were cultured as described above (Example 1) for 7 days with GMCSF+IL4 to produce myeloid dendritic cells (FIGS. 3A and 3C), or for 7 days in MCSF to produce macrophages (FIG. 3B) (Munn, D. H., et al., *J. Exp. Med.* 189: 1363-1372 (1999)). Prior to analysis, cells were treated with interferon-γ (INFγ) for 18 hrs to induce maximal expression of IDO. Harvested cells were triple-stained for CD123, CD11c and IDO. For FIG. 3D, cells were cultured as in Example 1 except in a commercial, FDA-approved serum-free medium formulation (X-vivo 15; BioWhitaker, Waldersville, Md.).

As shown in FIGS. 3A and B, both preparations contained a discrete subset of cells that expressed IDO following interferon-γ treatment. Characterization of these IDO$^+$ cells showed that they all expressed the myeloid-lineage marker CD11c, and CD 123, wherein>90% of the IDO$^+$ expressed the myeloid-lineage marker CD11c and >99% of the IDO$^+$ cells expressed CD123. To test whether these were truly DCs, additional phenotyping was performed. Cells were matured with TNFα during the last 2 days of culture, in order to upregulate maturation and costimulatory markers, and non-adherent cells were harvested. Following TNFα, all non-adherent cells displayed a veiled/dendritic morphology. Three-color phenotyping showed that the CD123$^+$/IDO$^+$ subset of cells were uniformly CD14$^-$ and CD83$^+$, consistent with their identity as dendritic cells; uniformly CD11b$^+$ and BDCA-2$^-$ (Dzionek, A., et al., *J. Immunol*, 165: 6037-6046 (2000)) consistent with their myeloid origin, and distinguishing them from plasmacytoid DCs (Grouard, G., et al., *J. Exp. Med.*, 185: 1101-1111 (1997)); and 100% positive for CD80, CD86 and MHC class II (HLA-DR). Under these conditions (bovine serum-based medium) CD11c expression was high on the CD123$^+$ subset, and was lower and variable on the CD123$^{LO}$ subset.

In addition, when monocytes were cultured under conditions that favored expression of CCR6 (serum-free medium, single-dose GMCSF+IL4), the CD123$^+$/IDO$^+$ cells were almost all (>99%) CCR6$^+$ (FIG. 3C). For experiments where CCR6 expression was of interest, cultures received a single dose of GMCSF+IL4 (100 ng/ml each) on day 0, with no further supplementation. Moreover, within the myeloid dendritic cell population, IDO and CCR6 expression were coincident. T and B cells, which also express CCR6, were excluded from analysis by forward and side scatter properties during flow cytometric analysis.

Expression of IDO is not found in all types of dendritic cells. Analysis of plasmacytoid dendritic cells, defined as the population of peripheral blood mononuclear cells expressing CD123 but negative for lineage-specific markers (Lin-1 marker cocktail, BD-Pharmingen), revealed no detectable expression of IDO following activation for 6 hrs or 24 hrs with interferon-γ, in the presence of IL3 to support viability (data not shown). Moreover, when the adherent cells (comprising the non-dendritic APC population) from cultures of peripheral blood mononuclear cells in GMCSF+IL4 were examined, they were found to express very low levels of IDO and little CD123 (FIG. 3D). Additional phenotyping of the non-dendritic APCs showed that they were uniformly CD14-positive and CD83-negative (thus, distinguishing them unambiguously from mature dendritic cells), but were >95% positive for CD80 and CD86 (thus, identifying them as mature antigen-presenting cells), and expressed high levels of the MHC class II antigen HLA-DR (further distinguishing them from immature dendritic cells, and identifying them as mature APCs). Consistent with the observed absence of IDO expression, these non-dendritic APCs showed excellent APC function without any detectable IDO-mediated suppression (i.e. no increase in proliferation in the presence of 1-methyl-(D)-typtophan (1-MT) (FIG. 3E), where stippled bars are standard MLR and striped bars are the MLR with 1-MT. The T cell: APC ratio in FIG. 5E was the same (20:1) for both DCs and non-dendritic APCs and both populations were isolated from the same culture of mononuclear cells in GMCSF+IL4 and tested against the same population of T cells in parallel MLRs.

Example 4

Figure 4:
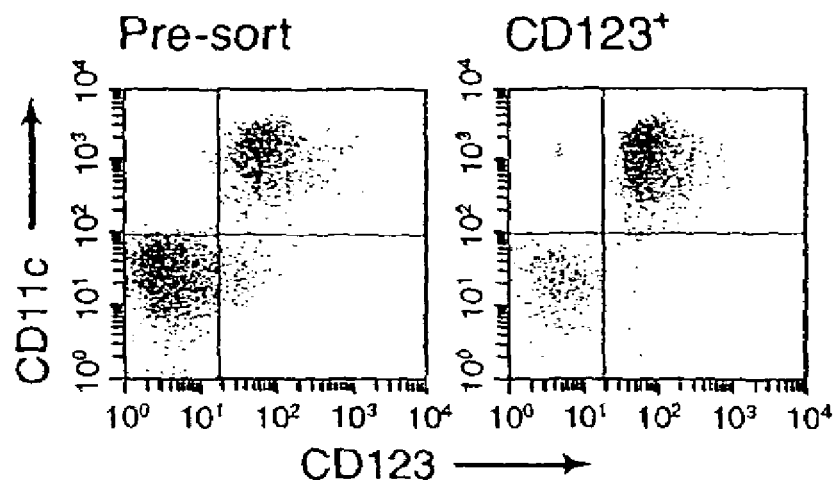
FIG. 4 shows suppression of allogeneic T cell proliferation by indoleamine 2,3-dioxygenase/CD123 expressing (IDO$^+$/CD123$^+$) dendritic cells in accordance with an embodiment of the present invention. Panel (A) shows myeloid dendritic cells which were activated for 24 hrs with TNFα, and labeled with anti-CD123 antibody and enriched by sorting (CD123$^+$) with goat anti-mouse secondary antibody conjugated to magnetic beads (immunosorting), wherein the left panel shows the population prior to enrichment and the right panel shows the population after enrichment. Panel (B) shows a comparison of the effect of CD123$^+$ enriched and CD123$^+$ depleted cells on allogeneic T cell proliferation as measured in a mixed-leukocyte reaction by thymidine incorporation in the absence (■) or the presence (□) of 1-methyl-(D,L)-tryptophan (1-MT; an inhibitor of IDO). Panel (C) shows experiments similar to panel (B), using 3 different pairs of donors, each allogeneic to the other, and each pair pre-tested to produce an active allogenic mixed leukocyte reaction (MLR) using sorted CD123$^+$ cells without (■) or with (□) 1-MT.
Figure 4:
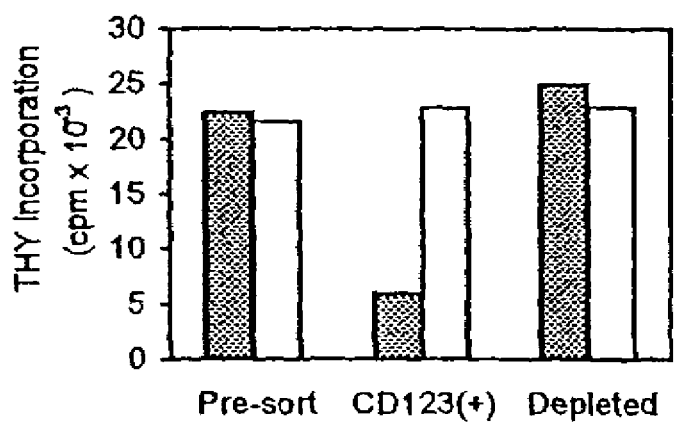
Figure 4:
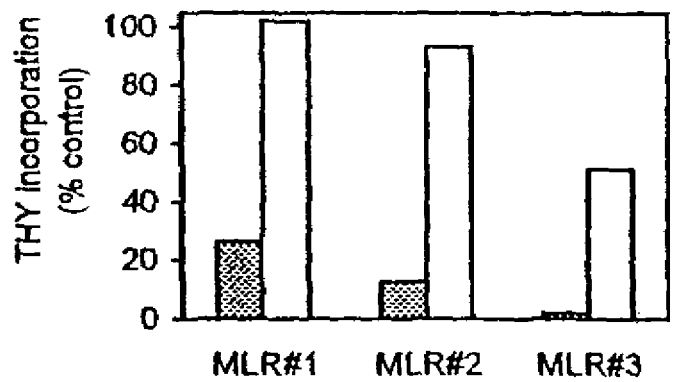

Suppression of Allogeneic T Cell Proliferation by Dendritic Cells Expressing IDO This experiment provides direct evidence that IDO expressing dendritic cells suppress allogeneic T cell proliferation (FIG. 4). Myeloid dendritic cells were activated for 24 hrs with TNFα (10 ng/ml, BD), labeled with anti-CD123 antibody, then enriched by sorting with goat anti-mouse secondary antibody conjugated to magnetic beads (Miltenyi Biotec). Since expression of cell-surface CD123 correlated closely with possession of inducible IDO, immunomagnetic sorting based on CD123 was used to enrich for the IDO$^+$ subset. Cells selected as CD123$^+$ cells (85-90% purity) by immunomagnetic sorting were then tested as stimulators in an allogeneic MLR. Dot-plots show analysis before ("Pre-sort") and after ("CD123$^+$") enrichment (FIG. 4A).

The CD123$^+$-enriched cells were used as APCs in an allogeneic MLR. Dendritic cells were mixed with purified allogeneic lymphocytes (<1% monocytes, 80-85% T cells, with the balance being B and natural killer (NK) cells) at a 1:10 ratio in V-bottom culture wells. After 5 days, proliferation was measured by 4 hr thymidine incorporation assay. Controls shown include the unfractionated population ("Pre-sort") and the cells remaining after positive selection for CD123 ("Depleted"). Typically <10% of the "Depleted" cell population was CD 123$^+$. Solid bars show conventional MLR; open bars show MLR in the presence of 200 uM 1-methyl-(D,L)-tryptophan (1-MT) (Sigma-Aldrich, St. Louis, Mo.), an inhibitor of IDO. In a similar set of experiments, 3 different pairs of donors, each allogeneic to the other, and each pair pre-tested to produce an active MLR were used without 1-MT (solid bars) or with 1-MT (open bars) (FIG. 4C).

As shown in FIGS. 4B and C, the CD123-enriched (CD123$^+$) (i.e., CCR6$^+$) IDO$^+$ cells were markedly less efficient at stimulating T cell proliferation than either the original unfractionated mixture, or than the CD123-depleted IDO$^{LO}$ subset that remained after sorting. To test the hypothesis that this lack of proliferation was due to active suppression by IDO, cultures were treated with 1-methyl-(D,L)-tryptophan (1-MT), a pharmacologic inhibitor of IDO. In the presence of 1-methyl-(D,L)-tryptophan, the CD123$^+$ dendritic cells stimulated proliferation at or near control levels (FIGS. 4B and C), demonstrating that IDO causes suppression.

It was found that immunosorting dendritic cells to select for CD123$^+$ (i.e., CCR6$^+$) cells results in a population of cells which exhibits high levels of IDO expression. In this experiment, monocyte derived dendritic cells (DCs) were labeled with anti-CD123 antibody and using immunomagnetic sorting. Immediately after sorting, cells were dual-stained for CD123 (surface) and IDO (intracellular). The positively selected cells were approximately 90% CD123$^+$. In addition, all (>99%) of the cells showed high levels of IDO as detected by staining. In contrast, the residual cells following CD123 depletion were mostly CD123 negative, and expressed low, or undetectable levels of IDO. Thus, it was found that the CD123 depleted population had 10-100 fold lower levels of IDO than the CD123$^+$ population. As expression of CD123$^+$ and CCR6$^+$ are highly correlated, these results indicate that CCR6$^+$ cell populations are also IDO$^+$.

Example 5

Detection of IDO-Expressing Dendritic Cells in Human Tumors and Tumor Draining Lymph Nodes This example shows that IDO$^+$ APCs are associated with human tumors and tumor draining lymph nodes (LNs). Samples of tumor and tumor-draining lymph nodes were chosen from patients with malignant melanoma, a tumor with well-defined T cell antigens but which nevertheless is not eliminated by the immune system. Recruitment of IDO$^+$ dendritic cells was also seen in carcinoma of the breast, lung, colon and pancreas, tumors which account for almost half of all cancer deaths in the United States.

Archival pathology specimens were stained for expression of IDO and other antigens by immunohistochemistry. Paraffin sections (5 um) were deparaffinized, treated for 8 min with proteinase K (Dako, Carpinteria, Calif.), and stained with rabbit anti-human IDO antibody (5 µg/ml in Tris buffered saline with 0.05% Tween-20 and 10% goat serum). Detection was via secondary antibody conjugated to alkaline phosphatase (LSAB-rabbit kit, Dako) with Fast Red chromogen, or horseradish peroxidase (LSAB2, Dako) and diaminobenzidine. Negative controls consisted of the anti-IDO antibody neutralized with a 100-fold molar excess of the immunizing peptide. Mip-3α (goat polyclonal, R&D Systems) was used following antigen retrieval with citrate (Target, Dako). For dual-staining, the first antibody was applied following appropriate antigen retrieval and detected with peroxidase/diaminobenzidine. Stained slides were then subjected to additional antigen retrieval if required and stained for the second antigen by alkaline phosphatase/Fast Red. Secondary antibodies were cross-adsorbed against mouse, human and bovine IgG for multiple labeling.

In all of these studies, the IDO+ cells observed appeared to be of the same cell type, displaying a characteristic morphology resembling plasmacytoid DCs (Cella, M., et al., *Nature Medicine* 5: 919-923 (1999)); Grouard, G., et al., *J. Exp. Med.*, 185: 1101-1111 (1997); Facchetti, F., et al., *J. Pathol.*, 158: 57-65 (1989)). They were neither histiocytic (macrophage-like) nor classically dendritic in appearance, and did not mark with Ham56 (a macrophage marker) or S100 (a marker of classical dendritic cells) (data not shown). Shown in FIG. 5A is a known positive control for detection of IDO (brown, diaminobenzidine chromogen) in syncytiotrophoblast cells of term human placenta (Kudo, Y., et al., *Biochem. Biophys. Acta* 1500: 119-124 (2000)). The inset shows the same tissue, but with anti-IDO antibody neutralized by an excess of the immunizing peptide. (Bar=100 um, inset at half-scale).

For normal lymphoid tissue controls, non-inflamed tonsil (from routine tonsillectomy, pathologic diagnosis of "hypertrophy") and lymph nodes from patients with node-negative breast cancer who never developed metastases or recurred in 5 years following resection were used. Although not technically "normal," these specimens were the least inflamed lymphoid tissue removed in routine clinical practice. Over 20 of these specimens have been examined, and they consistently show only rare, scattered IDO+ cells, usually localized to germinal centers (FIG. 5F).

For tumor-draining lymph nodes from regional lymph node dissections in patients with a variety of solid tumors (breast, colon, lung, and pancreatic carcinoma, and malignant melanoma) were used. Most of these nodes were not mapped by lymphoscintigraphy, so not all would actually drain the tumor, but many would. In all five types of tumor examined, a significant number of patients had one or more lymph nodes showing markedly abnormal collections of IDO+ cells (FIG. 5C). In these nodes, often massive infiltrates of IDO+ cells were localized to the perifollicular and interfollicular areas, often adjacent to the medullary sinuses, or collected in dense perivascular cuffs around high endothelial venules (FIG. 5D). In 328 lymph nodes from 26 patients with melanoma, abnormal infiltration of IDO+ cells was found in 14/26 patients. Where evidence suggestive of micro-metastases to lymph nodes was present, IDO+ cells often surrounded the margins of the tumor collections or melanin-laden macrophages (FIG. 5E).

Thus, FIG. 5C shows a draining lymph node of a malignant melanoma showing accumulation of IDO-expressing cells (red) in the lymphoid and perivascular regions of the node, but sparing the macrophage-rich sinuses (asterisk). (Bar=100 um). FIG. 5D shows a higher magnification of panel C, showing a characteristic collection of IDO-expressing cells around a high-endothelial venule (V). (Bar=50 um). FIG. 5E shows a low-power view of a draining lymph node containing heavily pigmented metastatic melanoma cells (endogenous melanin, black; darkest signal), with confluent infiltration of IDO-expressing cells (red; next darkest signal) around the tumor deposits.

For solid tumors, 14 malignant melanoma tumors were examined with 8/14 found to display collections of IDO+ cells at the site of the primary tumor. Usually these were in the connective tissue immediately surrounding the tumor (FIG. 5B, arrows) rather than in the tumor parenchyma itself. Similar infiltrates of IDO+ cells have been seen in breast, lung, and pancreatic tumors.

For inflamed lymphoid tissue tonsils known to be infected (either by clinical diagnosis or by histopathologic diagnosis) and lymph node biopsies bearing the histopathologic diagnosis of "reactive lymph node" were examined. Many of these specimens showed focal or regional collections of IDO+ cells. In tonsils these collections frequently occurred in a subepithelial location beneath the mucosa and along the crypts (not shown).

Finally, gut-associated lymphoid tissue from the (human) small intestine was examined since IDO+ DCs derived in vitro expressed CCR6, and mice with a targeted disruption of CCR6 (Varona, R., et al., *J. Clin. Invest.*, 107: R37-45 (2001)) fail to recruit a population of myeloid DCs into the lymphoid tissue of the gut. FIG. 5G shows prominent collections of IDO+ cells in the lamina propria overlying lymphoid aggregates in the gut, congregating near cells expressing mip-3α (the ligand for CCR6 (Sozzani, S. et al., *J. Leukocyte Biol.* 66: 1-9 (1999); Zlotnik, A., et al., *Immunity* 12: 121-127 (2000)).

It was found that cells expressing IDO co-localized with cells expressing mip-3α Sections of normal human small intestine were used as a positive control for mip-3α expression, since murine studies have shown that mip-3α is highly expressed in the subepithelial tissues overlying mucosal lymphoid aggregates of the small intestine (A. Iwasaki and B. L. Kelsall, *J. Exp. Med.* 191: 1381-1394 (2000)). As shown in FIG. 5G, the corresponding region in humans contained focal collections of cells expressing mip-3α, along with extensive co-localization of IDO-expressing dendritic cells to the same areas. Thus, FIGS. 5G and H shows co-localization of cells expressing IDO (brown; darkest cytoplasmic signal) and mip-3α (red; next darkest signal) in the lamina propria of the small intestine, particularly in the subepithelial areas overlying mucosal lymphoid aggregates (LA). FIG. 8H shows a higher magnification of the region in panel G indicated by the arrow. Bar=50 um.

Examination of mip-3α expression in malignancies showed that many primary and metastatic tumors contained individual tumor cells (FIG. 5I) or entire localized regions within the tumor that expressed mip-3α by immunohistochemistry. Although both mip-3α and IDO expressing cells are found in the tumor, they did not appear to be located in identical cells. Thus, FIG. 5I shows expression of mip-3α (red) (arrow, lower right) by tumor cells in a lesion of malignant melanoma metastatic to lymph node. The mip-3α+ cells are scattered throughout the tumor (T), while the IDO+ cells are congregated at the margins of the metastasis but confined to the residual lymph node tissue (LN). FIG. 5J shows a higher magnification of the region in panel M indicated by the arrow, showing mip-3α expression in tumor cells where the bar=50 um.

In addition, the morphology of these cells showed that they were tumor cells, not stroma or other host-derived cells. Quantitative analysis of mip-3α mRNA by real-time PCR confirmed expression in 8/18 samples of malignant melanoma (see Example 7). To ensure that this was not an idiosyncratic property of melanomas, additional RNA samples were analyzed from tumors of unrelated histology and cell of origin (renal cell carcinoma and non-small cell lung cancer). This confirmed that a variety of tumor types express mip-3α (D. Bell et al., *J. Exp. Med.* 190, 1417-1426 (1999)).

Example 6

IDO+ Cells are Prognostic of a Poor Clinical Outcome

Melanoma patients were chosen for prognostic evaluation, because it is routine clinical practice to determine the first tumor-draining LN ("sentinel node") at the time of surgery (using dye and lymphoscintigraphy studies) and thus, there was a high certainty that the identified LNs were truly tumor-draining nodes. An analysis of 40 patients for whom long-term (5-10 year) outcome was known, and for whom the original sentinel LN specimen had been prospectively obtained and archived, was performed. Samples were generously provided by collaborators at the Moffitt Cancer Center. Because host immunologic factors were being determined, patients were included only if the tumor-draining LN was free of any detectable metastases at the time of diagnosis. In all patients, the primary tumor was completely resected and no further therapy was given. Of 40 LNs studied, 12 had abnormal accumulation of IDO$^+$ cells. As determined by Kaplan-Meier survival analysis (not shown), the presence of IDO$^+$ cells was a definite adverse prognostic factor, which reached statistical significance ($p<0.05$).

This experiment indicated that the recruitment of IDO$^+$ cells occurred prior to the first detectable metastasis. Also, this experiment indicates that these cells may be predictive of a poor outcome, perhaps because they are mechanistically involved in creating the state of tolerance that allows eventual dissemination.

Example 7

Quantification of Mip-3α Expression in Human Tumors

It was found that human tumors express mip-3α. RNA was isolated from melanomas (M, n=18), renal cell carcinomas (R, n=19) or non-small cell lung cancers (L, n=9) and analyzed for expression of mip-3α by quantitative RT-PCR (FIG. 6). The RNA was reverse-transcribed using random hexamer priming and analyzed using the LightCycler real-time PCR system (Roche, Indianapolis, Ind.) and FastStart DNA Amplification Kit (SYBR Green 1, Roche). The primers used were: GAPDH (GenBank GI:7669491, sense basepairs (bp) 87-104, antisense bp 289-307) and mip-3α (GenBank GI:4759075, sense bp 103-121, antisense bp 410-428). Standard curves were prepared from U937 cells induced with phorbol myristate acetate for 24 hrs, and were linear (r=−0.99) in the range of 100 pg to 100 ng total RNA.

It was found that there was an increase in mip-3α mRNA in all three tumor types assayed (FIG. 6). To permit comparison between different samples the data are presented as an index, calculated as the ratio of mip-3α to the GAPDH housekeeping gene in each sample, normalized to the value of the control cell line (resting U937 cells). The data shown thus represent fold increase of mip-3α expression over that for GAPDH.

Example 8

Mip-3α Induces Chemotaxis of CCR6$^+$ APCs

In this experiment, mip-3α-induced chemotaxis of CCR6$^+$/IDO$^+$ APCs was measured. Dendritic cells matured with a cytokine cocktail as described herein were used for a chemotaxis assay with mip-3α as the chemoattractant. Thus, monocytes were cultured in serum free medium (X-Vivo15) for five days in the presence of GMCSF (50 ng/mL) and IL-4 (50 ng/mL). After five days, cells were treated with a cytokine cocktail consisting of IL-1β (1870 U/mL), IL-6 (1000 U/mL), TNFα (1100 U/mL) and prostaglandin E$_2$ (PGE$_2$; 1.0 µg/mL), for two days. The cells were harvested and used for the chemotaxis assay. Control starting DCs were immunostained for CD123 and CCR6 ("Pre-Chemotaxis DCs").

Mip-3α (0.5 µg/mL) was added to the different chambers and a defined number of DCs (0.5×10$^6$/well) were put on the upper chamber. After 4 hours, cells were counted in lower chamber of each group (Table 2). FACS immunostain was performed on all groups for CCR6 and CD123 (FIG. 7). FACS immunostain demonstrated selective migration of CCR6$^+$ DCs induced by mip-3α (Table 2; FIG. 7). Migration required a gradient of mip-3α from the upper chamber to the lower chamber, consistent with ligand induced chemotaxis.

TABLE 2

| Number of Dendritic Cells After Migration | | |
|---|---|---|
| Addition to Upper Chamber | Addition to Lower Chamber | Number of Cells in Lower Chamber |
| None | None | 0.17 |
| Mip-3α | None | 0.73 |
| None | Mip-3α | 2.96 |
| Mip-3α | Mip-3α | 0.98 |

Two distinct populations (CCR6$^{LO}$/CD123$^{LO}$ and CCR6$^+$/CD123$^+$) were measured in the starting population of DCs. Thus, as shown in FIG. 7, pre-chemotaxis DCs comprise a mixed population of DCs showing low expression of CCR6 and CD123 (lower left quadrant) and high levels of CCR6 and CD123 (upper right quadrant). Cells which migrate in response to mip-3α (DCs after chemotaxis) are enriched for DCs expressing high levels of CCR6 and CD123.

Example 9

Mip-3α Induced Chemotaxis of CCR6$^+$ APCs is Blocked by CCR6 Antibody

Monocyte-derived human dendritic cells (adherent and non-adherent fractions) were harvested and pooled, as described in Example 8, yielding a preparation comprising a mixture of both CD123-positive (CCR6-positive) and CD123-negative (CCR6-negative) cells. In Example 8, it was shown that a gradient of mip-3α caused selective migration of the CD123+ (CCR6+) population. To test the hypothesis that this migration was specifically caused by the binding of mip-3α to the CCR6 receptor, migration studies with and without a blocking antibody against the CCR6 molecule were conducted. It is known in the art that that blocking antibodies against chemokine receptors can prevent receptor-induced migration, thus demonstrating the specificity of a particular ligand for a specific receptor.

The mixed population of DCs was allowed to migrate across a porous membrane in response to a gradient of mip-3alpha, as described in Example 8. Different treatment groups received a commercial anti-CCR6 antibody (10 ug/ml), an isotype-matched control antibody at the same concentration, or no antibody. After 18 hrs, migrating cells (recovered in the lower chamber of the chemotaxis assay apparatus) were harvested, counted, and analyzed by flow cytometry for CD123 expression. CD123 was used as a marker to identify the IDO-expressing population, rather than CCR6, because the anti-CCR6 blocking antibody could artifactually interfere with immunofluorescent staining for CCR6. Since both markers are co-expressed on the IDO+ cells with a one-to-one correspondence, either marker gives equivalent information.

FIG. 8 shows a representative set of results from such an assay. Only the CD123+ population (i.e., the population expressing CCR6) showed any significant differential migration in response to a mip-3α gradient. The CD123-negative cells showed a small amount of constitutive migration, but there was little effect of mip-3α, so this was not specific ligand-induced chemotaxis. In response to a gradient of mip-3α, migration of CD123+ cells was increased >10-fold. This differential migration enriched the migrated population to 96% pure CD123+ cells (from a starting population of only 68% CD123+). Mip-3α induced migration was substantially reduced when the mip-3α was present on both sides of the membrane (instead of in a gradient), indicating that the majority of the migration was true gradient-induced chemotaxis (not simply chemokinesis).

When an irrelevant control antibody was added to this system, it had little effect on migration (control: i.e., the fourth set of bars). However, when anti-CCR6 antibody was added (fifth set of bars) it almost completely abrogated the mip-3α-specific migration—the inhibitory effect of anti-CCR6 is shown by the arrow in the figure. The CCR6 antibody was not itself toxic, because there were ample CD123$^+$ cells recovered in the upper (non-migrated) population at the end of the assay (54-58% of unmigrated cells were CD123$^+$ at the end of the assay, which was comparable to the controls receiving no mip-3alpha and no anti-CCR6 antibody.) Thus, this experiment shows that the selective migration of the CD123$^+$ (IDO-expressing) subset of cells in response to mip-3alpha can be prevented by a blocking agent which targets CCR6.

Example 10

IDO$^+$ APCs Infiltrate HIV-Infected Lymphoid Tissue

Figure 9:
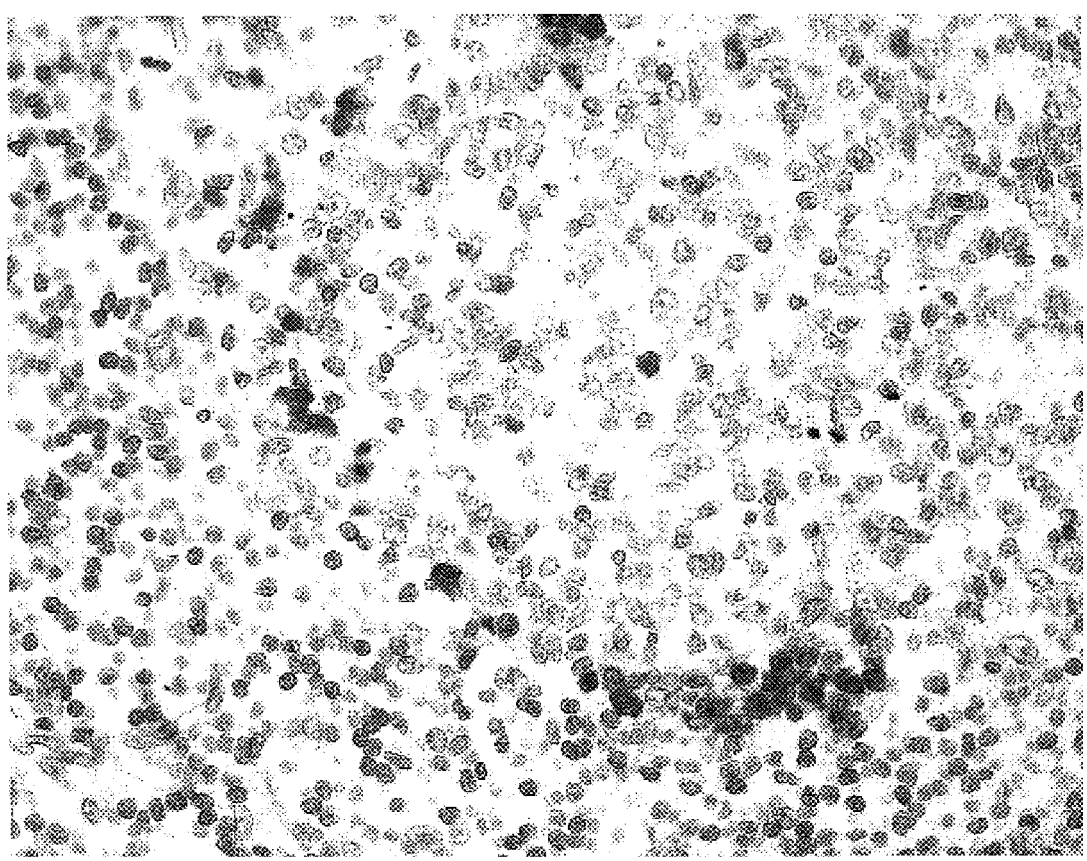
FIG. 9 shows IDO$^+$ APCs in HIV-infected lymphoid tissue in accordance with an embodiment of the present invention.

FIG. 9 shows lymphoid tissue (tonsil) from a patient with HIV infection showing infiltration of IDO$^+$ cells (red) (regions of dark staining in black and white photo) into the T cell areas of the lymphoid follicle (40× magnifications). Methods of tissue staining are as in Example 5. By comparison, $15/16$ normal (non-infected) tonsils showed rare or no detectable IDO$^+$ cells (with $1/16$ having scattered collections of IDO$^+$ cells, but much fewer than the patient shown with HIV). Heavy infiltrates of IDO$^+$ cells in lymph nodes and tonsils from HIV-infected patients is consistently found, indicating that these tolerogenic APCs contribute to the immunosuppressed state seen in HIV.

Example 11

IDO$^+$ Cells are Selectively Recruited into Mouse Tumor-Draining Lymph Nodes

To determine the phenotype of IDO$^+$ cells in mouse tumor-draining lymph nodes (LNs), C57BL/6 mice were implanted in the hind limb with syngeneic B16F10 melanoma cells. After 10-14 days of tumor growth (such that the tumor was about 5 mm diameter), the animals were sacrificed and the tumor-draining LNs and contralateral LNs removed for histology. FIG. 11A shows that there was significant accumulation of IDO$^+$ cells in the draining LN of B16F10 tumors, and that these cells were not present in the contralateral LNs of the same animals (FIG. 11D).

The LNs harvested from B16F10 were too small to yield sufficient IDO$^+$ cells for functional analysis. Therefore, a GMCSF-transfected sub-line of B16 (B78H1/GMCSF, referred to herein as B78.GM (obtained from collaborators at the Moffit Cancer Center) was implanted in the hind limb of the mice. When these tumors were allowed to grow for 12-14 days, their draining LNs were found to be significantly larger that B16F10 (FIG. 11E). Although the B78.GM LNs were not qualitatively different from the other tumor-draining LNs examined (B16F10, the parental B78H1 line, or Lewis lung carcinoma (LLC)), in that they recruited the same population of IDO$^+$ cells (i.e., same morphology and in the same in hilar and subcapsular distribution), the LNs from the B78.GM tumors quantitatively yielded ~10 times more cells than other lymph nodes.

Example 12

IDO$^+$ APCs in Tumor-Draining LNs are B220$^+$ CD11c$^+$ pDCs

The LNs comprising IDO$^+$ cells were analyzed to determine the type of APCs present. LNs from mice with B78.GM tumors were disaggregated, sorted, and stained for IDO by cytospins. FIG. 11C shows that >90% of cells in the B220$^+$ CD11c$^+$ (plasmacytoid) DC subset were constitutively IDO$^+$. Comparison with the "non-pDC" (all other cells) population from the same sorting run revealed that IDO expression was confined to the B220$^+$ CD11c$^+$ subset. Based on CTLA4-Ig challenge of normal mice, the B220$^+$ pDCs were one of the two subsets predicted to be "IDO-competent" (data not shown). However, it is noteworthy that in the tumor-draining nodes, these pDCs were constitutively activated to express IDO, requiring no exogenous stimulation. Initial 4-color phenotyping indicates that the majority of the B220$^+$CD11c$^+$ pDCs are Ly6C$^+$ (95%), CD8α$^+$ (59%), CD45RB$^{HIGH}$ (99%) and CD11b$^+$ (69%) (not shown).

Example 13

Suppressor Activity is Selectively Localized to Tumor-Draining Lymph Nodes

Lymph node (LN) cells were harvested from inguinal LNs draining established B78.GM tumors. Control cells were harvested from the contralateral inguinal nodes in the same mouse. LN cells were irradiated and used as stimulators in allo-MLRs, with the responder cells being TCR-transgenic CD8$^+_b$ T cells from BM3 mice, as BM3 T cells recognize H-2K$^b$ as an alloantigen (Tarazona, R., et al., *Int. Immunol.*, 8:351-358, (1996)), and thus are reactive with all MHC class I positive cells from C57BL/6 tumor-bearing hosts. These cells are known by those of skill in the art to be a recognized assay system for IDO-mediated suppression of the T cell response (Munn, D. H., et al., *Science*, 297:1867-1870, (2002); Lee et al., *Immunol.*, 107:1-9, (2002)). As shown in FIG. 12A, the draining LN cells (DLN) were very poor stimulators in MLR (no detectable stimulation over background). In contrast, the contralateral (non-tumor-draining) LNs (CLN) from the same animals were excellent stimulators (comparable to cells taken from a non-tumor-bearing mouse). Mixing experiments revealed that the lack of stimulation by the draining LN cells was due to the presence of a dominant suppressor activity in those nodes, which was not present in the contralateral LNs (FIG. 12B).

Example 14

IDO-Mediated Suppression in Tumor-Draining Lymph Nodes Segregates with IDO$^+$ APCs To determine the etiology of T cell suppression by APCs, tumor draining lymph node cells were harvested from B78.GM tumors and sorted into a B220$^+$ CD11c$^+$ plasmacytoid dendritic cell (pDC) fraction and a CD25$^+$CD4$^+$ regulatory T-cell (Treg) fraction. A third "all other" fraction was also collected. Each fraction was used as stimulators in an MLR with BM3 responders. In each group, a replicate, identical MLR received 1MT to block IDO. Pooled draining LN cells (4 nodes) were stained and fractionated by 4-color cell sorting for the two populations shown in the top schematic. All other cells were collected in a third fraction. Each fraction was then used as stimulators in MLRs (FIG. 13), using 50,000 BM3 T cells as responders. The number of stimulators used in each MLR was adjusted to be the same as would have been present in 50,000 cells of the original LN preparation, based on the measured percentage of each sorted fraction. Thus, in the experiment shown, 500 cells of the sorted B220+ CD11c+ fraction were added per well, and 1500 cells of the CD25+ CD4+ fraction, while 48,000 cells of the "all other" fraction were used. Replicate MLRs were performed with, or without, 1MT as shown.

FIG. 13A shows that the "all other" fraction of cells (depleted of both regulatory populations) stimulated T cell proliferation. Stimulation was not enhanced by 1MT, indicating that there was no IDO-mediated suppression present in the "all other" fraction.

In contrast, the B220+ CD11c+ (pDC) fraction was potently inhibitory (FIG. 13A). That this was IDO mediated inhibition (rather than simply a lack of antigen-presenting ability) was demonstrated by the fact that suppression was fully reversed by adding 1MT. Mixing experiments (i.e., B220+ CD11c+ pDCs plus the "all other" fraction) showed that IDO-mediated suppression was dominant, and was again fully reversed by adding 1MT. This result indicates that the only difference between an inhibitory pDC and a stimulatory pDC was whether or not IDO was active. Thus, IDO was not merely "associated" with the suppressive pDC phenotype, it was the direct causative mechanism of suppression by these cells. The CD25+ CD4+ (Treg) fraction also showed inhibition (which was also dominant in mixing experiments). However, the suppression mediated by Tregs was not affected by 1 MT, (as expected) since Tregs do not express IDO.

Thus, the tumor-draining LNs contained two suppressor activities: (1) the direct suppression mediated by IDO+ pDCs, and (2) an IDO-independent component of suppression mediated by Tregs. This finding of regulatory pDCs and regulatory T cells together in the tumor-draining LN is consistent with the model proposed in FIG. 10.

FIG. 13B shows the same experiment as in FIG. 13A, but using LNs taken from an IDO-knockout (IDO-KO) host. In these mice, inhibition by the pDC fraction was completely absent (i.e., there was no suppression when pDCs were mixed with the "all other" group. There was also no enhancing effect of 1MT in any group, confirming the specificity of 1MT as an IDO inhibitor. While the IDO-mediated component of inhibition was absent in the knockout mice, there was still a clear component of suppression by Tregs. Still, although tumors in the IDO-KO may be able to recruit a population of pre-existing, centrally-derived Tregs, they are not able to use IDO to create new specificities of Tregs.

It will be understood that each of the elements described above, or two or more together, may also find utility in applications differing from the types described. While the invention has been illustrated and described as methods and compositions for reducing immune tolerance, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as described herein.

---

---

That which is claimed is:

1. A method to reduce recruitment of IDO+ dendritic cells that inhibit T-cell proliferation to at least one of a tumor or a tumor-draining lymph node in a subject comprising administering a composition comprising an antibody to CCR6 to the subject, wherein the IDO+ dendritic cells express CCR6 and elevated levels of indoleamine 2,3-dioxygenase (IDO), and tumor cells of the at least one of a tumor or a tumor draining lymph node express MIP-3a.

2. The method of claim 1, wherein the subject is human.

3. The method of claim 1, wherein the CCR6 antibody blocks the interaction between the CCR6 expressed by the IDO+ dendritic cells and the MIP-3α expressed by tumor cells of the at least one of a tumor or a tumor draining lymph node.

4. The method of claim 1, further comprising the step of determining that IDO+ dendritic cells are recruited to the at least one of a tumor or a tumor-draining lymph node.

5. The method of claim 1, wherein the MIP-3α mediates recruitment of the IDO+ dendritic cells to the at least one of a tumor or a tumor draining lymph node.

* * * * *